(12) United States Patent
Bugianesi et al.

(10) Patent No.: US 7,479,504 B2
(45) Date of Patent: Jan. 20, 2009

(54) EDG RECEPTOR AGONISTS

(75) Inventors: Robert L. Bugianesi, Brick, NJ (US); George A. Doherty, Princeton, NJ (US); Amy Gentry, Sutton (GB); Jeffrey J. Hale, Westfield, NJ (US); Christopher L. Lynch, Scotch Plains, NJ (US); Sander G. Mills, Scotch Plains, NJ (US); William E. Neway, III, Newton, PA (US)

(73) Assignee: Merck & Co., Inc., Rahway, NJ (US)

(*) Notice: Subject to any disclaimer, the term of this patent is extended or adjusted under 35 U.S.C. 154(b) by 519 days.

(21) Appl. No.: 10/500,895

(22) PCT Filed: Jan. 15, 2003

(86) PCT No.: PCT/US03/01196
§ 371 (c)(1),
(2), (4) Date: Jul. 7, 2004

(87) PCT Pub. No.: WO03/062252
PCT Pub. Date: Jul. 31, 2003

(65) Prior Publication Data
US 2005/0033055 A1 Feb. 10, 2005

Related U.S. Application Data

(60) Provisional application No. 60/350,000, filed on Jan. 18, 2002.

(51) Int. Cl.
*A61K 31/4025* (2006.01)
*C07D 205/04* (2006.01)
*C07D 409/12* (2006.01)

(52) U.S. Cl. ............ 514/422; 548/950; 548/953; 548/527

(58) Field of Classification Search .......... 548/950, 548/953, 527; 514/422
See application file for complete search history.

(56) References Cited

U.S. PATENT DOCUMENTS

| 5,495,046 | A | 2/1996 | Nakazato et al. |
| 5,597,825 | A | 1/1997 | Himmelsbach et al. |
| 6,437,165 | B1 | 8/2002 | Mandala et al. |
| 7,179,823 | B1 * | 2/2007 | Momose et al. ............. 514/341 |
| 2002/0042443 | A1 | 4/2002 | Day et al. |

FOREIGN PATENT DOCUMENTS

| WO | WO 96/05193 | 2/1996 |
| WO | WO 98/06694 | 2/1998 |
| WO | WO 01/38325 A1 | 5/2001 |

OTHER PUBLICATIONS

The Journal of Biological Chemistry, vol. 275, No. 19, Issue of May 12, pp. 14281-14286, 2000.

* cited by examiner

*Primary Examiner*—Rebecca L Anderson
(74) *Attorney, Agent, or Firm*—Yong Zhao; Valerie J. Camara

(57) ABSTRACT

The present invention encompasses compounds of Formula 1: as well as the pharmaceutically acceptable salts and hydrates thereof. The compounds are useful for treating immune mediated diseases and conditions, such as bone marrow, organ and tissue transplant rejection. Pharmaceutical compositions and methods of use are included.

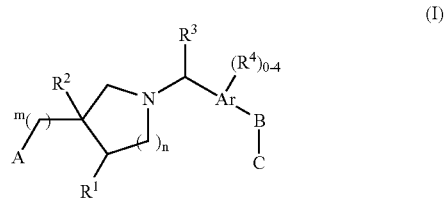

(I)

5 Claims, No Drawings

EDG RECEPTOR AGONISTS

CROSS REFERENCE TO RELATED APPLICATIONS

This application is a U.S. National Phase application under 35 U.S.C. § 371 of PCT Application No. US03/01196, filed Jan. 15, 2003, which claims priority under 35 U.S.C. 119 to U.S. Ser. No. 60/350,000, filed Jan. 18, 2002.

BACKGROUND OF THE INVENTION

The present invention is related to compounds that are $S1P_1$/Edg1 receptor agonists and thus have immunosuppressive activities by producing lymphocyte sequestration in secondary lymphoid tissues. The invention is also directed to pharmaceutical compositions containing such compounds and methods of treatment or prevention.

Immunosuppressive agents have been shown to be useful in a wide variety of autoimmune and chronic inflammatory diseases, including systenic lupus erythematosis, chronic rheumatoid arthritis, type I diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, autoimmune myositis, Wegener's granulomatosis, ichthyosis, Graves ophthalmopathy, atopic dermatitis and asthma. They have also proved useful as part of chemotherapeutic regimens for the treatment of cancers, lymphomas and leukemias.

Although the underlying pathogenesis of each of these conditions may be quite different, they have in common the appearance of a variety of autoantibodies and/or self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce both cellular and humoral responses including antibodies, cytokines and cytotoxic lymphocytes which lead to graft rejection.

One end result of an autoimmune or a rejection process is tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophospharide, act in such a nonspecific fashion that both the normal and autoimmune responses are shut off. Indeed, patients treated with such nonspecific immunosuppressive agents are as likely to succumb to infection as they are to their autoimmune disease.

Cyclosporin A is a drug used to prevent rejection of transplanted organs. FK-506 is another drug approved for the prevention of transplant organ rejection, and in particular, liver transplantation. Cyclosporin A and FK-506 act by inhibiting the body's immune system from mobilizing its vast arsenal of natural protecting agents to reject the transplant's foreign protein. Cyclosporin A was approved for the treatment of severe psoriasis and has been approved by European regulatory agencies for the treatment of atopic dermatitis.

Though they are effective in delaying or suppressing transplant rejection, Cyclosporin A and FK-506 are known to cause several undesirable side effects including nephrotoxicity, neurotoxicity, and gastrointestinal discomfort. Therefore, an immunosuppressant without these side effects still remains to be developed and would be highly desirable.

The immunosuppressive compound FTY720 is a lymphocyte sequestration agent currently in clinical trials. FTY720 is metabolized in mammals to a compound that is a potent agonist of sphingosine 1-phosphate receptors. Agonism of sphingosine 1-phosphate receptors induces the sequestration of lymphocytes (T-cells and B-cells) in lymph nodes and Peyer's patches without lymphodepletion. Such immunosuppression is desirable to prevent rejection after organ transplantation and in the treatment of autoimmune disorders.

Sphingosine 1-phosphate is a bioactive sphingolipid metabolite that is secreted by hematopoietic cells and stored and released from activated platelets. Yatomi, Y., T. Ohmori, G. Rile, F. Kazama, H. Okamoto, T. Sano, K. Satoh, S. Kume, G. Tigyi, Y. Igarashi, and Y. Ozaki. 2000. *Blood*. 96:3431-8. It acts as an agonist on a family of G protein-coupled receptors to regulate cell proliferation, differentiation, survival, and motility. Fukushima, N., I. Ishii, J. J. A. Contos, J. A. Weiner, and J. Chun. 2001. Lysophospholipid receptors. Annu. Rev. Pharmacol. Toxicol. 41:507-34; Hla, T., M.-J. Lee, N. Ancellin, J. H. Paik, and M. J. Kluk. 2001. Lysophospholipids—Receptor revelations. *Science*. 294:1875-1878; Spiegel, S., and S. Milstien. 2000. Functions of a new family of sphingosine-1-phosphate receptors. *Biochim. Biophys. Acta*. 1484: 107-16; Pyne, S., and N. Pyne. 2000. Sphingosine 1-phosphate signalling via the endothelial differentiation gene family of G-protein coupled receptors. *Pharm. & Therapeutics*. 88:115-131. Five sphingosine 1-phosphate receptors have been identified ($S1P_1$, $S1P_2$, $S1P_3$, $S1P_4$, and $S1P_5$, also known as endothelial differentiation genes Edg1, Edg5, Edg3, Edg6, Edg8), that have widespread cellular and tissue distribution and are well conserved in human and rodent species (see Table). Binding to S1P receptors elicits signal transduction through Gq-, Gi/o, G12-, G13-, and Rho-dependent pathways. Ligand-induced activation of $S1P_1$ and $S1P_3$ has been shown to promote angiogenesis, chemotaxis, and adherens junction assembly through Rac- and Rho-, see Lee, M.-J., S. Thangada, K. P. Claffey, N. Ancellin, C. H. Liu, M. Kluk, M. Volpi, R. I. Sha'afi, and T. Hla. 1999. *Cell*. 99:301-12, whereas agonism of $S1P_2$ promotes neurite retraction, see Van Brocklyn, J. R., Z. Tu, L. C. Edsall, R. R. Schmidt, and S. Spiegel. 1999. *J. Biol. Chem*. 274:4626-4632, and inhibits chemotaxis by blocking Rac activation, see Okamoto, H., N. Takuwa, T. Yokomizo, N. Sugimoto, S. Sakurada, H. Shigematsu, and Y. Takuwa. 2000. *Mol. Cell. Biol*. 20:9247-9261. $S1P_4$ is localized to hematopoietic cells and tissues, see Graeler, M. H., G. Bernhardt, and M. Lipp. 1999. *Curr. Top. Microbiol. Immunol*. 246:131-6, whereas $S1P_5$ is primarily a neuronal receptor with some expression in lymphoid tissue, see Im, D. S., C. E. Heise, N. Ancellin, B. F. O'Dowd, G. J. Shei, R. P. Heavens, M. R. Rigby, T. Hla, S. Mandala, G. McAllister, S. R. George, and K. R. Lynch. 2000. *J. Biol. Chem*. 275:14281-6. Administration of sphingosine 1-phosphate to animals induces systemic sequestration of peripheral blood lymphocytes into secondary lymphoid organs, stimulates FGF-mediated blood vessel growth and differentiation, see Lee, et al., supra, but also has cardiovascular effects that limit the utility of sphingosine 1-phosphate as a therapeutic agent, see Sugiyama, A., N. N. Aye, Y. Yatomi, Y. Ozaki, and K. Hashimoto. 2000. *Jpn. J. Pharmacol*. 82:338-342. The reduced heart rate and blood pressure measured with sphingosine 1-phosphate is associated with its non-selective, potent agonist activity on all S1P receptors.

The present invention encompasses compounds which are agonists of the $S1P_1$/Edg1 receptor having selectivity over the $S1P_3$/Edg3 receptor. An $S1P_1$/Edg1 receptor selective agonist has advantages over current therapies and extends the therapeutic window of lymphocytes sequestration agents, allowing better tolerability with higher dosing and thus improving efficacy as monotherapy.

While the main use for immunosuppressants is in treating bone marrow, organ and transplant rejection, other uses for such compounds include the treatment of arthritis, in particular, rheumatoid arthritis, insulin and non-insulin dependent diabetes, multiple sclerosis, psoriasis, inflammatory bowel disease, Crohn's disease, lupus erythematosis and the like.

Thus, the present invention is focused on providing immunosuppressant compounds that are safer and more effective than prior compounds. These and other objects will be apparent to those of ordinary skill in the art from the description contained herein.

| Summary of S1P receptors | | | |
|---|---|---|---|
| Name | Synonyms | Coupled G proteins | mRNA expression |
| S1P$_1$ | Edg1, LP$_{B1}$ | G$_{i/o}$ | Widely distributed, endothelial cells |
| S1P$_2$ | Edg5, LP$_{B2}$, AGR16, H218 | G$_{i/o}$, G$_q$, G$_{12/13}$ | Widely distributed, vascular smooth muscle cells |
| S1P$_3$ | Edg3, LP$_{B3}$ | G$_{i/o}$, G$_q$, G$_{12/13}$ | Widely distributed, endothelial cells |
| S1P$_4$ | Edg6, LP$_{C1}$ | G$_{i/o}$ | Lymphoid tissues, lymphocytic cell lines |
| S1P$_5$ | Edg8, LP$_{B4}$, NRG1 | G$_{i/o}$ | Brain, spleen |

SUMMARY OF THE INVENTION

The present invention encompasses compounds of Formula I:

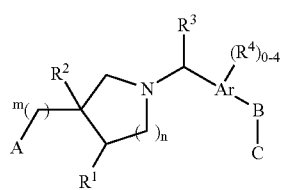

(I)

as well as the pharmaceutically acceptable salts and hydrates thereof. The compounds are useful for treating immune mediated diseases and conditions, such as bone marrow, organ and tissue transplant rejection. Pharmaceutical compositions and methods of use are included.

DETAILED DESCRIPTION OF THE INVENTION

The present invention encompasses compounds represented by Formula I:

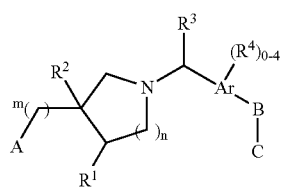

(I)

or a pharmaceutically acceptable salt or hydrate thereof, wherein:
Ar is phenyl or naphthyl;

m=0 or 1;
n=0 or 1;
A is selected from the group consisting of: —CO$_2$H, —PO$_3$H$_2$, —PO$_2$H, —SO$_3$H, —PO(C$_{1-3}$alkyl)OH and 1H-tetrazol-5-yl;

R$^1$ and R$^2$ are each independently selected from the group consisting of: hydrogen, halo, hydroxy, —CO$_2$H and C$_{1-4}$alkyl, optionally substituted from one up to the maximum number of substitutable positions with halo;

R$^3$ is selected from the group consisting of: hydrogen and C$_{1-4}$alkyl, optionally substituted with from one up to the maximum number of substitutable positions with a substituent independently selected from the group consisting of: halo and hydroxy;

each R$^4$ is independently selected from the group consisting of: halo, C$_{1-4}$alkyl and C$_{1-3}$alkoxy, said C$_{1-4}$alkyl and C$_{1-3}$alkoxy optionally substituted from one up to the maximum number of substitutable positions with halo, C is selected from the group consisting of:
(1) C$_{1-8}$alkyl, C$_{1-8}$alkoxy, —(C═O)—C$_{1-6}$alkyl or —CHOH—C$_{1-6}$alkyl, said C$_{1-8}$alkyl, C$_{1-8}$alkoxy, —(C═O)—C$_{1-6}$alkyl and —CHOH—C$_{1-6}$alkyl optionally substituted with phenyl, and
(2) phenyl or HET, each optionally substituted with 1-3 substituents independently selected from the group consisting of: halo, phenyl, C$_{1-4}$alkyl and C$_{1-4}$alkoxy, said C$_{1-4}$alkyl and C$_{1-4}$alkoxy groups optionally substituted from one up to the maximum number of substitutable positions with a substituent independently selected from halo and hydroxy, and said phenyl optionally substituted with 1 to 5 groups independently selected from the group consisting of: halo and C$_{1-4}$alkyl, optionally substituted with 1-3 halo groups, or C is not present;

when C is not present then B is selected from the group consisting of: phenyl, C$_{5-16}$alkyl, C$_{5-16}$alkenyl, C$_{5-16}$alkynyl, —CHOH—C$_{4-15}$alkyl, —CHOH—C$_{4-15}$alkenyl, —CHOH—C$_{4-15}$alkynyl, C$_{4-15}$alkoxy, —O—C$_{4-15}$alkenyl, —O—C$_{4-15}$alkynyl, C$_{4-15}$alkylthio, —S—C$_{4-15}$alkenyl, —S—C$_{4-15}$alkynyl, —CH$_2$—C$_{3-14}$alkoxy, —CH$_2$—O—C$_{3-14}$alkenyl, —CH$_2$—O—C$_{3-14}$alkynyl, —(C═O)—C$_{4-15}$alkyl, —(C═O)—C$_{4-15}$alkenyl, —(C═O)—C$_{4-15}$alkynyl, —(C═O)—O—C$_{3-14}$alkyl, —(C═O)—O—C$_{3-14}$alkenyl, —(C═O)—O—C$_{3-14}$alkynyl, —(C═O)—N(R$^6$)(R$^7$)—C$_{3-14}$alkyl, —(C═O)—N(R$^6$)(R$^7$)—C$_{3-14}$alkenyl, —(C═O)—N(R$^6$)(R$^7$)—C$_{3-14}$alkynyl, —N(R$^6$)(R$^7$)—(C═O)—C$_{3-14}$alkyl, —N(R$^6$)(R$^7$)—(C═O)—C$_{3-14}$alkenyl and —N(R$^6$)(R$^7$)—(C═O)—C$_{3-14}$alkynyl, when C is phenyl or HET then B is selected from the group consisting of: C$_{1-6}$alkyl, C$_{1-5}$alkoxy, —(C═O)—C$_{1-5}$alkyl, —(C═O)—O—C$_{1-4}$alkyl, —(C═O)—N(R$^6$)(R$^7$)—C$_{1-4}$alkyl,

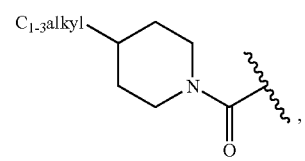

when C is C$_{1-8}$alkyl, C$_{1-8}$alkoxy, —(C═O)—C$_{1-6}$alkyl or —CHOH—C$_{1-6}$alkyl then B is phenyl; and R$^6$ and R$^7$ are independently selected from the group consisting of: hydrogen, C$_{1-9}$alkyl and —(CH$_2$)$_p$-phenyl, wherein p is 1 to 5 and phenyl is optionally substituted with 1-3 substituents independently selected from the group consisting of: $C_{1-3}$alkyl and $C_{1-3}$alkoxy, each optionally substituted with 1-3 halo groups.

An embodiment of the invention encompasses a compound of Formula I wherein:

Ar is phenyl;

the group —B—C is attached to the phenyl ring at the 3- or 4-position;

C is phenyl or HET, each optionally substituted with 1-3 substituents independently selected from the group consisting of: halo, phenyl, $C_{1-4}$alkyl and $C_{1-4}$alkoxy, said $C_{1-4}$alkyl and $C_{1-4}$alkoxy groups optionally substituted from one up to the maximum number of substitutable positions with a substituent independently selected from halo and hydroxy, and said phenyl optionally substituted with 1 to 5 groups independently selected from the group consisting of: halo and $C_{1-4}$alkyl, optionally substituted with 1-3 halo groups, or C is not present;

when C is not present then B is selected from the group consisting of: $C_{7-12}$alkyl, $C_{7-12}$alkenyl, $C_{7-12}$alkynyl, $C_{6-11}$alkoxy, —O—$C_{6-11}$alkenyl, —O—$C_{6-11}$alkenyl, —(C=O)—$C_{6-11}$alkyl, —(C=O)—$C_{6-11}$alkenyl, —(C=O)—$C_{6-11}$alkynyl, —(C=O)—O—$C_{5-10}$alkyl, (C=O)—O—$C_{5-19}$alkenyl, and —(C=O)—O—$C_{5-10}$alkynyl and C is not present; and when C is phenyl or HET then B is selected from the group consisting of $C_{1-5}$alkyl, $C_{1-4}$alkoxy, —(C=O)—$C_{1-4}$alkyl, —(C=O)—O—$C_{1-3}$alkyl, phenyl and HET.

For purposes of this specification, when the group —B—C is attached to the phenyl ring at the 3- or 4-position, it means the positions shown in the following:

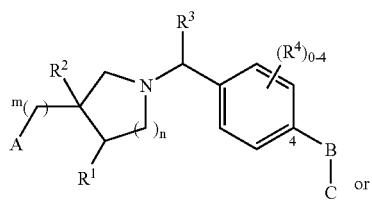

or

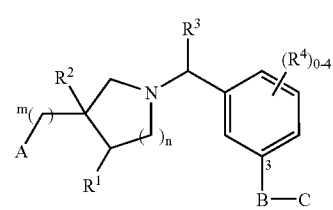

For purposes of this specification, C may be substituted at any substitutable position on B. For example, when B is methoxy and C is thiophene, thiophene replaces a hydrogen on the methoxy group. Further variations are illustrated in the examples that follow. Also, the point of any attachments shown for B is to the Ar group. For example, when B is —(C=O)—$C_{6-11}$alkynyl this means B is attached to Ar as follows: Ar—(C=O)—$C_{6-11}$alkynyl. C may then be substituted at any substituable position on B.

An embodiment of the invention encompasses the compound of Formula I wherein HET is selected from the group consisting of:

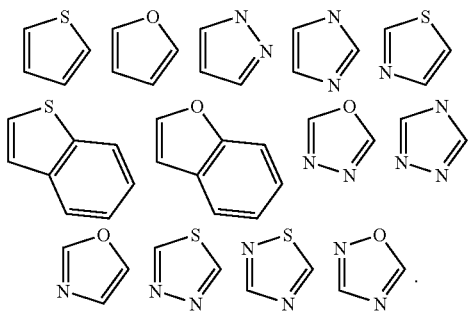

Another embodiment encompasses the compound of Formula I wherein m is 0.

Another embodiment encompasses the compound of Formula I wherein m is 1.

Another embodiment encompasses the compound of Formula I wherein n is 0.

Another embodiment encompasses the compound of Formula I wherein n is 1.

Another embodiment encompasses the compound of Formula I wherein B is selected from the group consisting of: $C_{7-12}$alkyl, $C_{7-12}$alkenyl, $C_{7-12}$alkynyl, $C_{6-11}$alkoxy, —O—$C_{6-11}$alkenyl, —O—$C_{6-11}$alkynyl, —(C=O)—$C_{6-11}$alkyl, —(C=O)—$C_{6-11}$alkenyl, —(C=O)—$C_{6-11}$alkynyl, —(C=O)—O—$C_{5-10}$alkyl, —(C=O)—O—$C_{5-19}$alkenyl, and —(C=O)—O—$C_{5-10}$alkynyl and C is not present;

Another embodiment of the invention encompasses the compound of Formula I wherein: B is methoxy and C is HET substituted with phenyl and $C_{1-4}$alkyl, said $C_{1-4}$alkyl optionally substituted from one up to the maximum number of substitutable positions with halo, and said phenyl, optionally substituted with 1 to 5 substituents independently selected from the group consisting of: halo and $C_{1-4}$alkyl, optionally substituted with 1-3 halo groups. Within this embodiment is encompassed the compound of Formula I wherein C is selected from the group consisting of:

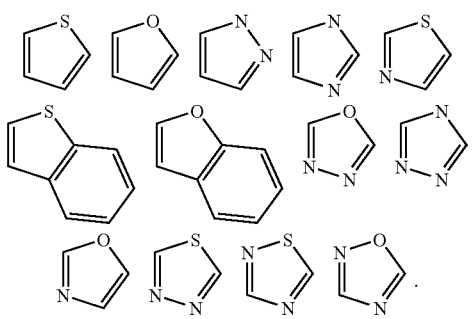

Also encompassed is a compound of Formula I wherein C is thiophene or furan.

Another embodiment of the invention encompasses the compound of Formula I wherein: B is methoxy and C is HET. Within this embodiment is encompassed the compound of Formula I wherein C is selected from the group consisting of:

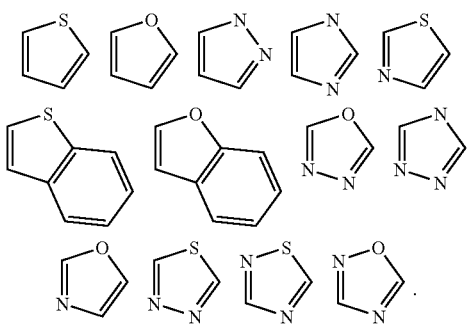

Also within this embodiment is encompassed the compound of Formula I wherein C is benzothiophene or benzofuran.

Another embodiment of the invention encompasses the compound of Formula I wherein: B is methoxy and C is phenyl substituted with two $C_{1-4}$alkyl groups, said $C_{1-4}$alkyl optionally substituted from one up to the maximum number of substitutable positions with halo.

Another embodiment of the invention encompasses the compound according to claim 1 wherein: B is HET and C is HET substituted with phenyl and $C_{1-4}$alkyl, said $C_{1-4}$alkyl optionally substituted from one up to the maximum number of substitutable positions with halo, and said phenyl optionally substituted with 1 to 5 substituents independently selected from the group consisting of: halo, $C_{1-4}$alkyl, optionally substituted with 1-3 halo groups. Within this embodiment is encompassed the compound of Formula I wherein B is 1,2,4-oxadiazole. Also within this embodiment is encompassed the compound of Formula I wherein B is 1,2,4-oxadiazole C is selected from the group consisting of:

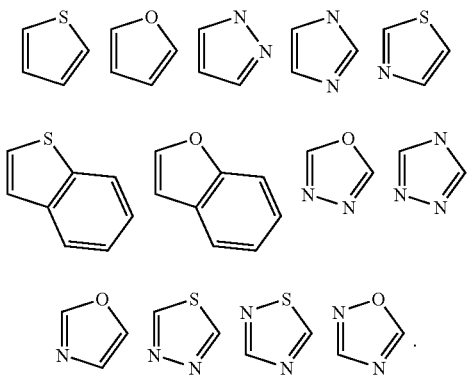

Also within this embodiment is encompassed the compound of Formula I wherein B is 1,2,4-oxadiazole and C is thiophene or furan.

Another embodiment of the invention encompasses the compound of Formula I wherein m=0 and A is —$CO_2H$. Within this embodiment is encompassed the compound of Formula I wherein $R^1$, $R^2$ and $R^3$ are hydrogen.

Another embodiment of the invention encompasses the compound of Formula I wherein the group —B—C is attached to the phenyl ring at the 4-position.

The invention also encompasses a compound represented by Formula II

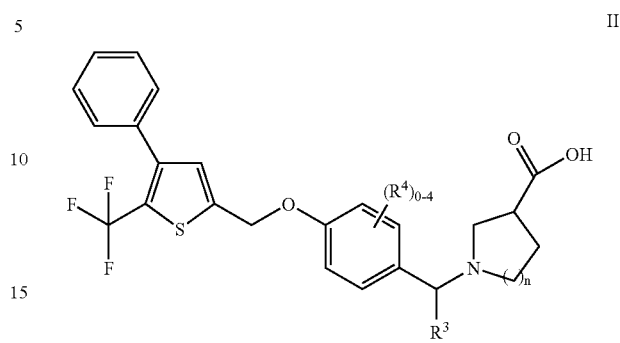

or a pharmaceutically acceptable salt or hydrate thereof, wherein:

n=0 or 1;

$R^3$ is selected from the group consisting of: hydrogen and $C_{1-4}$alkyl, optionally substituted with from one up to the maximum number of substitutable positions with a substituent independently selected from the group consisting of: halo and hydroxy;

each $R^4$ is independently selected from the group consisting of: halo, $C_{1-4}$alkyl and $C_{1-3}$alkoxy, said $C_{1-4}$alkyl and $C_{1-3}$alkoxy optionally substituted from one up to the maximum number of substitutable positions with halo.

Another embodiment of the invention encompassed a compound of Formula II wherein n is 0.

Another embodiment of the invention encompassed a compound of Formula II wherein n is 1.

Another embodiment of the invention encompassed a compound of Formula II wherein $R^3$ is hydrogen.

The invention also encompasses a compound represented by Formula III

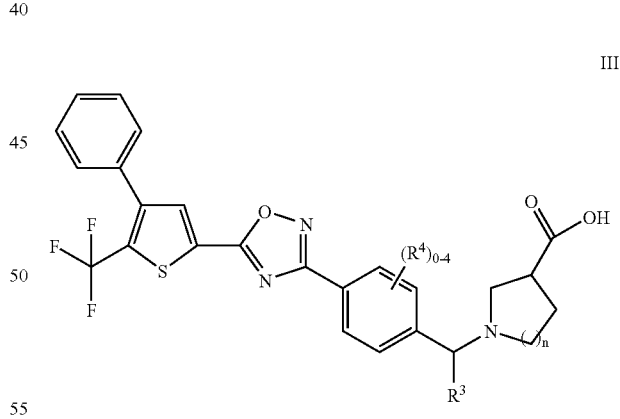

or a pharmaceutically acceptable salt or hydrate thereof, wherein:

n=0 or 1;

$R^3$ is selected from the group consisting of: hydrogen and $C_{1-4}$alkyl, optionally substituted with from one up to the maximum number of substitutable positions with a substituent independently selected from the group consisting of: halo and hydroxy;

each $R^4$ is independently selected from the group consisting of: halo, $C_{1-4}$alkyl and $C_{1-3}$alkoxy, said $C_{1-4}$alkyl and C$_{1-3}$alkoxy optionally substituted from one up to the maximum number of substitutable positions with halo.

Another embodiment of the invention encompassed a compound of Formula III wherein n is 0.

Another embodiment of the invention encompassed a compound of Formula III wherein n is 1.

Another embodiment of the invention encompassed a compound of Formula II wherein R$^3$ is hydrogen.

The invention also encompasses a method of treating an immunoregulatory abnormality in a mammalian patient in need of such treatment comprising administering to said patient a compound of Formula I in an amount that is effective for treating said immunoregulatory abnormality.

Within this embodiment is encompassed the above method wherein the immunoregulatory abnormality is an autoimmune or chronic inflammatory disease selected from the group consisting of: systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

Also within this embodiment is encompassed the above method wherein the immunoregulatory abnormality is bone marrow or organ transplant rejection or graft-versus-host disease.

Also within this embodiment is encompassed the above method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C$_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection Also within this embodiment is encompassed the above method wherein the immunoregulatory abnormality is multiple sclerosis Also within this embodiment is encompassed the above method wherein the immunoregulatory abnormality is rheumatoid arthritis Also within this embodiment is encompassed the above method wherein the immunoregulatory abnormality is systemic lupus erythematosus Also within this embodiment is encompassed the above method wherein the immunoregulatory abnormality is psoriasis Also within this embodiment is encompassed the above method wherein the immunoregulatory abnormality is rejection of transplanted organ or tissue Also within this embodiment is encompassed the above method wherein the immunoregulatory abnormality is inflammatory bowel disease.

Also within this embodiment is encompassed the above method wherein the immunoregulatory abnormality is a malignancy of lymphoid origin including acute and chronic lymphocytic leukemias and lymphomas.

The invention also encompasses a method of suppressing the immune system in a mammalian patient in need of immunosuppression comprising administering to said patient an immunosuppressing effective amount of a compound of Formula I.

The invention also encompasses a pharmaceutical composition comprised of a compound of Formula I in combination with a pharmaceutically acceptable carrier.

Exemplifying the invention are the following compounds:
| Example No. | Structure |
|---|---|
| 1 | 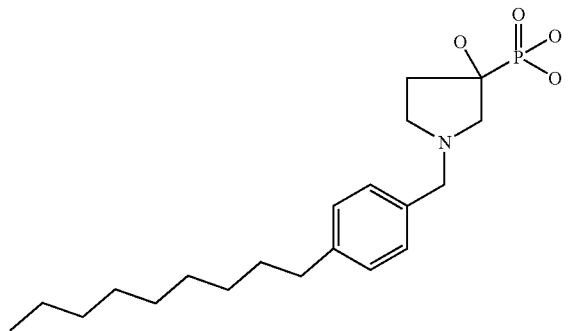 |
| 2 | 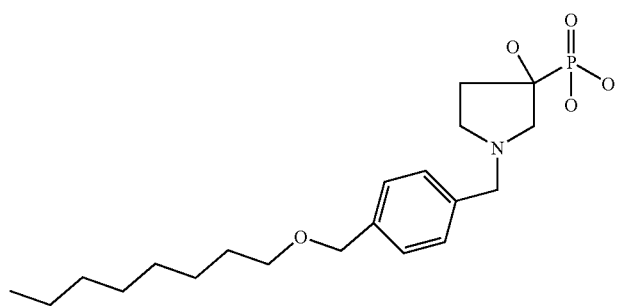 |
| 3 | 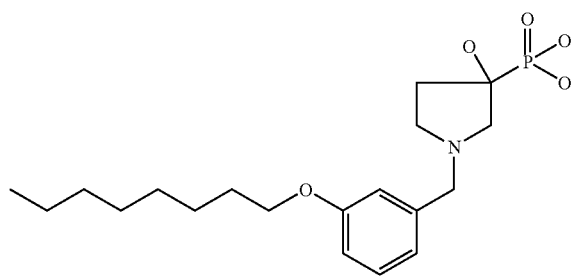 |
| 4 | 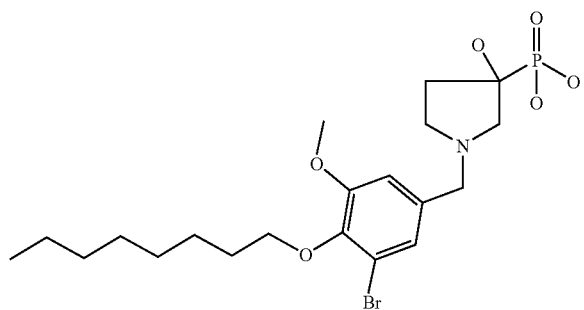 |
| 5 + 6 | 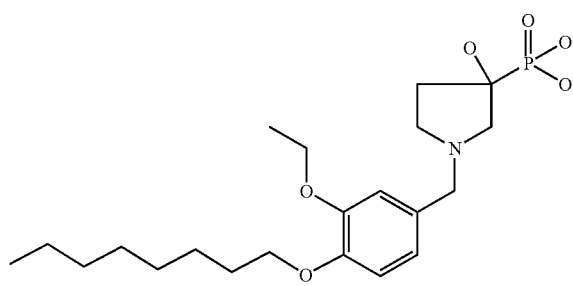 |

-continued
| Example No. | Structure |
|---|---|
| 7 | 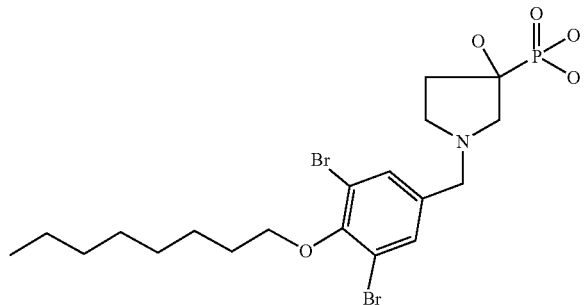 |
| 8 | 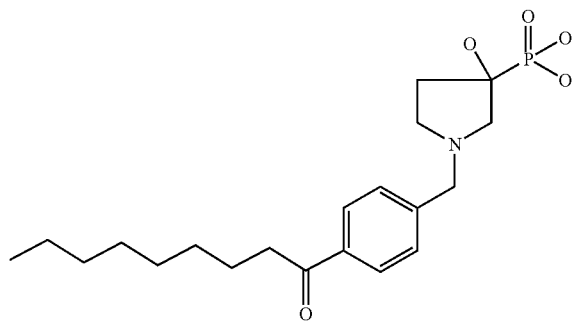 |
| 9 | 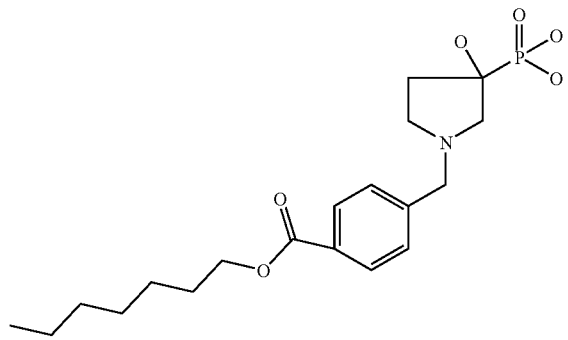 |
| 10 | 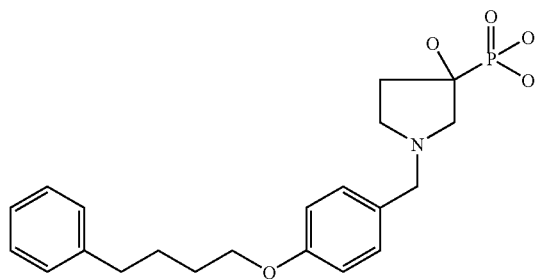 |

-continued
| Example No. | Structure |
|---|---|
| 11 | 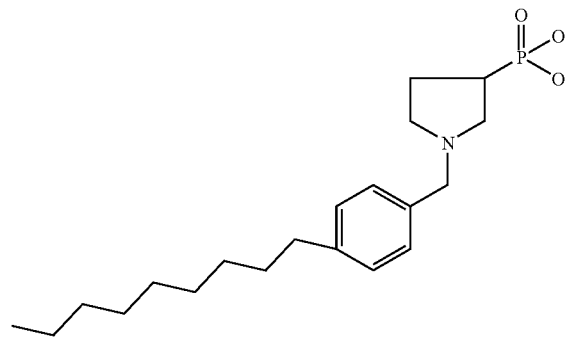 |
| 12 | 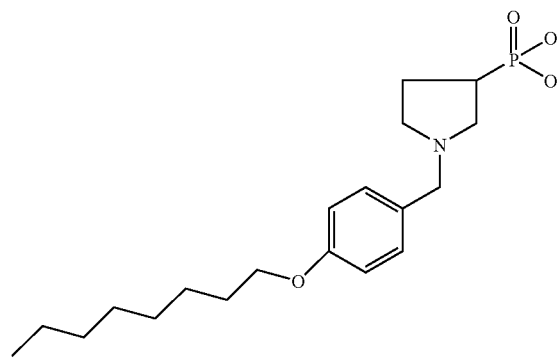 |
| 13 | 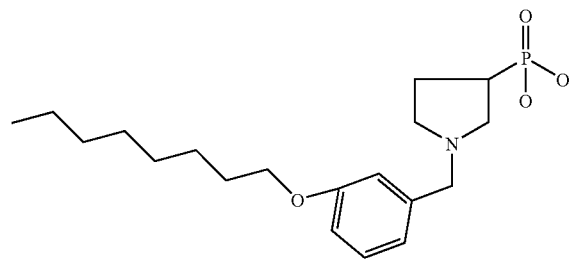 |
| 14 | 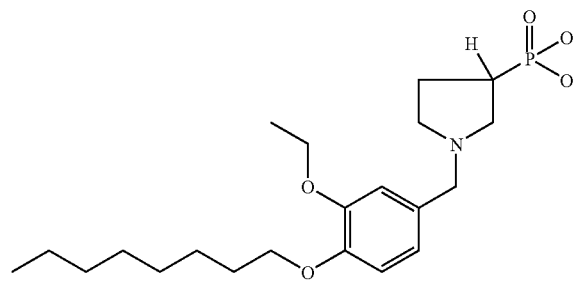 |
| 15 + 16 | 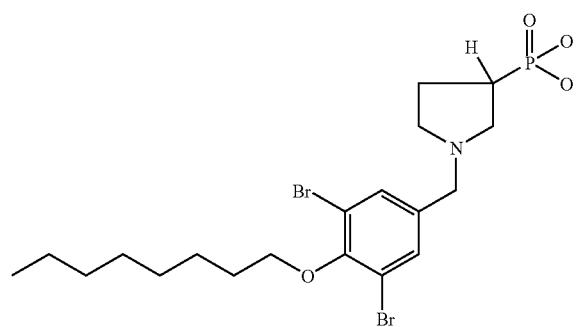 |

-continued
| Example No. | Structure |
|---|---|
| 17 | 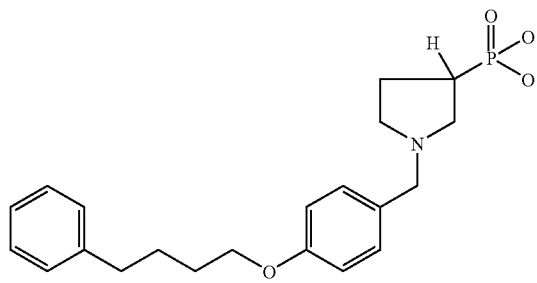 |
| 18 | 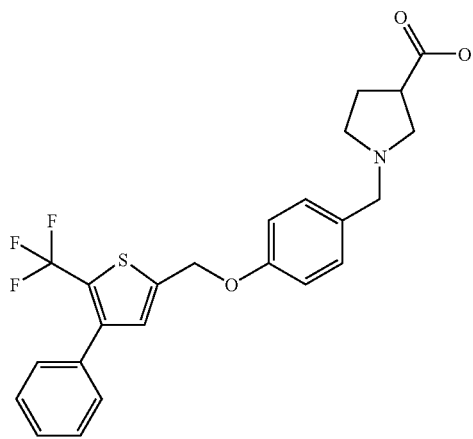 |
| 19 | 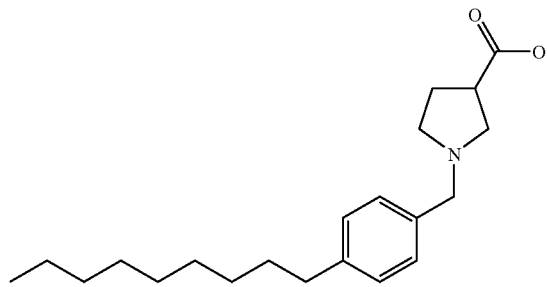 |
| 20 | 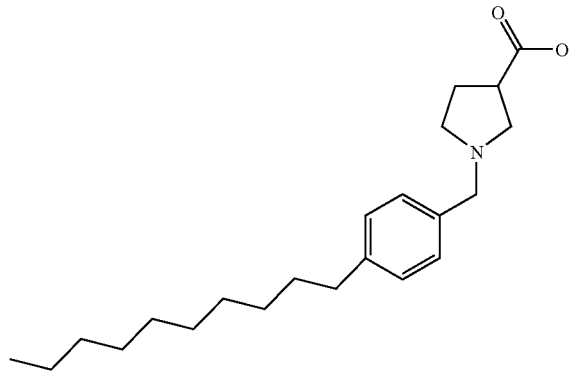 |

-continued
| Example No. | Structure |
|---|---|
| 21 | 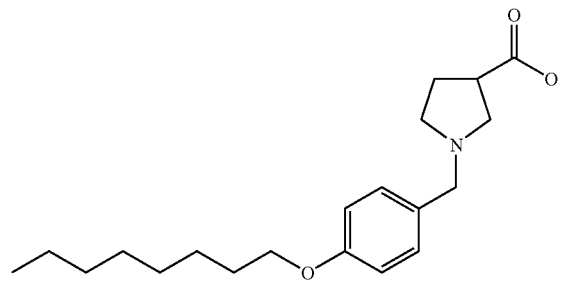 |
| 22 | 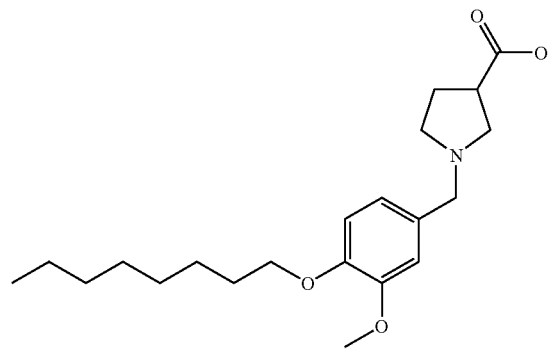 |
| 23 | 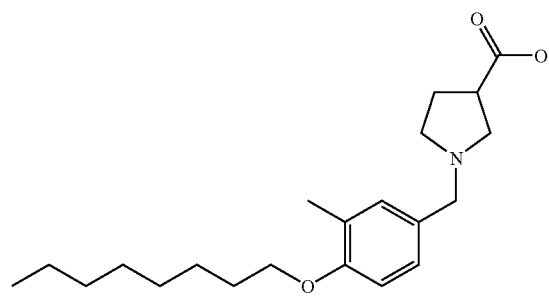 |
| 24 | 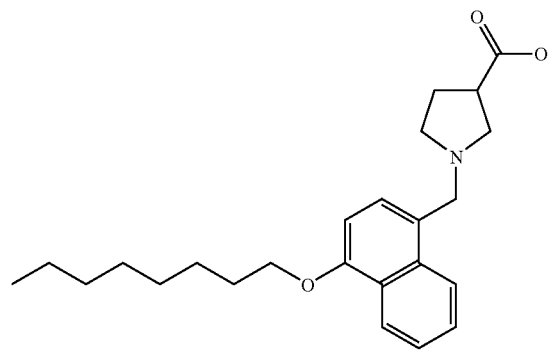 |
| 25 | 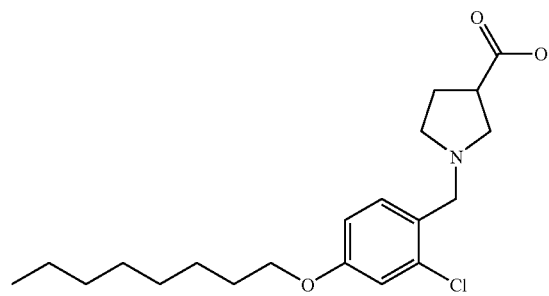 |

-continued
| Example No. | Structure |
|---|---|
| 26 | 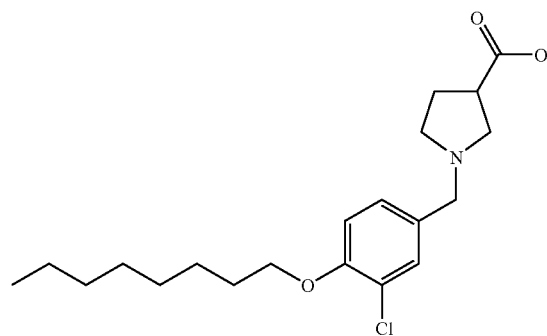 |
| 27 | 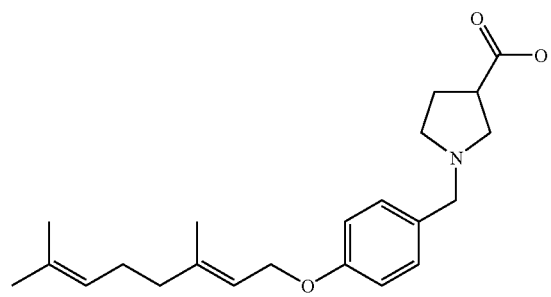 |
| 28 | 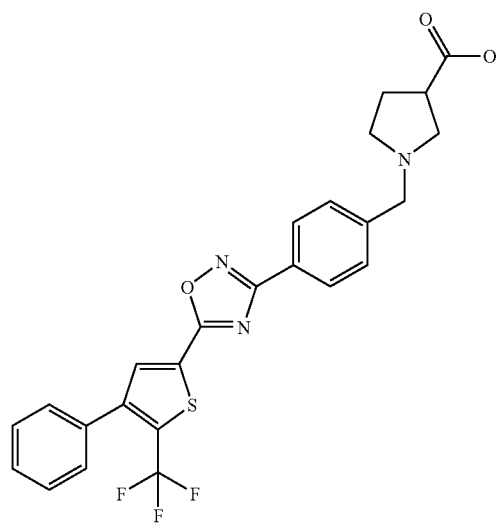 |
| 29 | 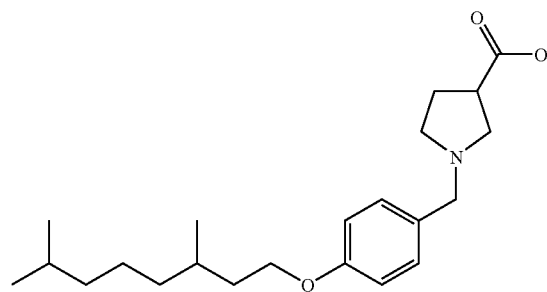 |

-continued
| Example No. | Structure |
|---|---|
| 30 | 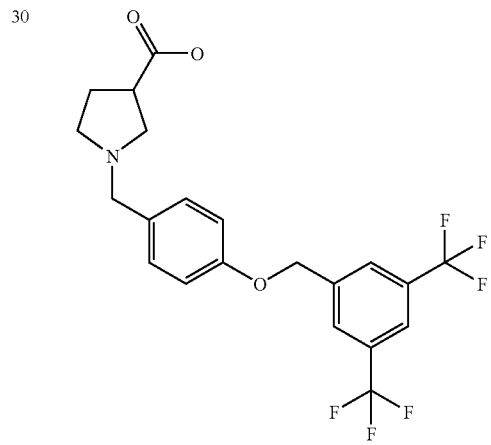 |
| 31 | 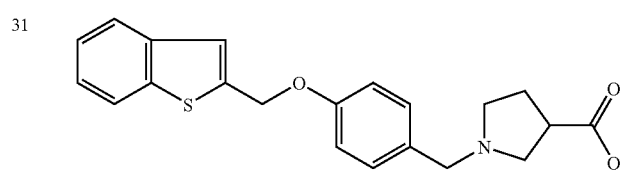 |
| 32 | 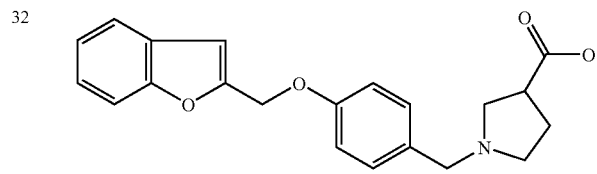 |
| 33 | 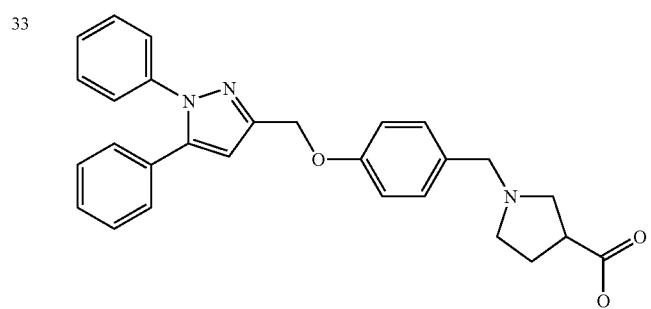 |
| 35 | 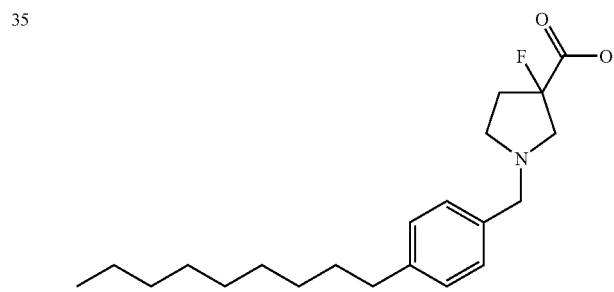 |

-continued
| Example No. | Structure |
|---|---|
| 36 | 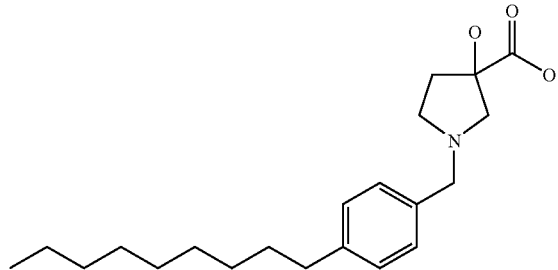 |
| 37 | 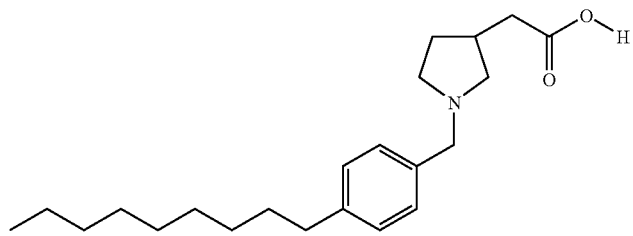 |
| 38 | 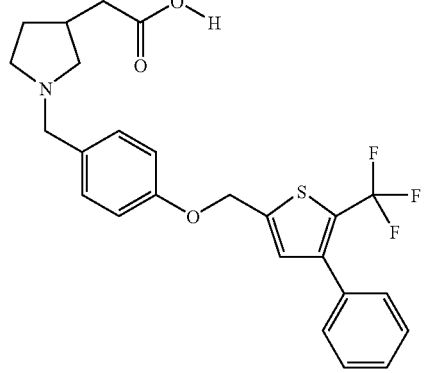 |
| 39 | 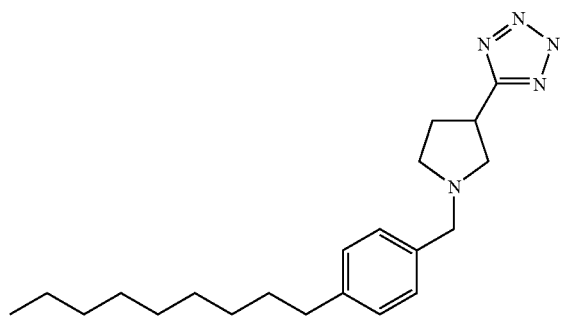 |
| 40 | 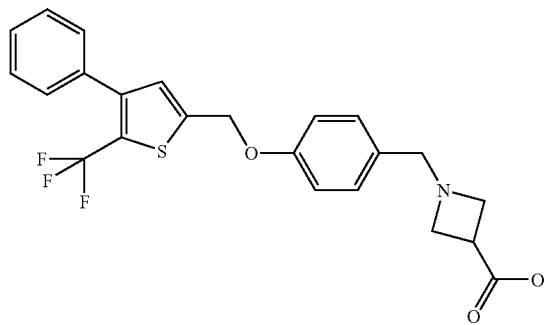 |

-continued
| Example No. | Structure |
|---|---|
| 41 | 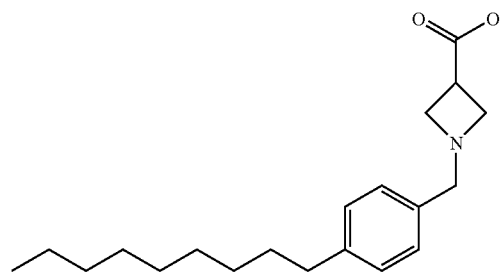 |
| 42 | 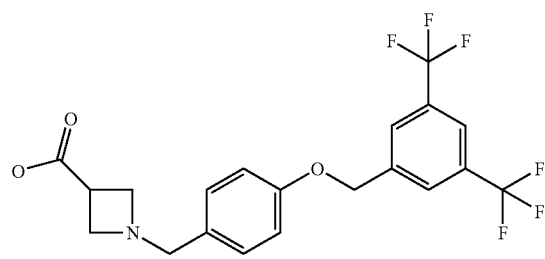 |
| 43 | 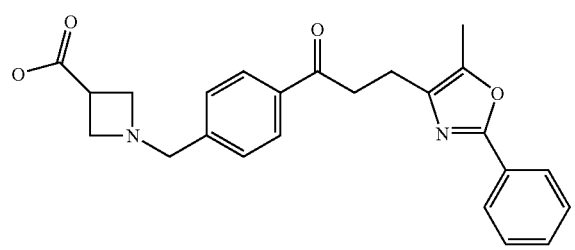 |
| 44 | 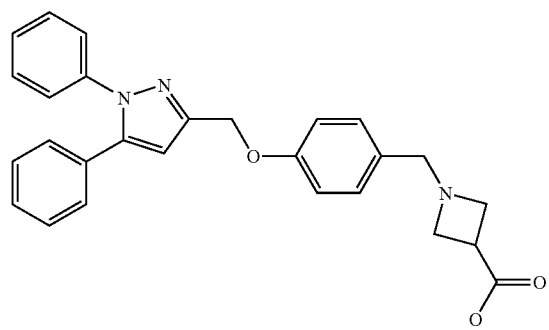 |
| 45 | 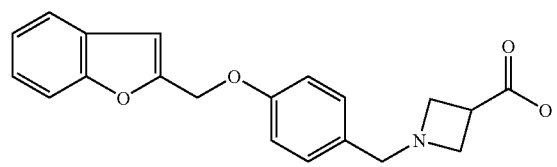 |
| 46 | 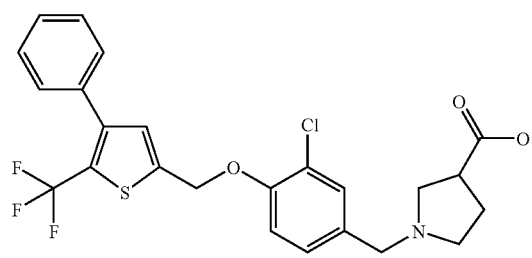 |

-continued
| Example No. | Structure |
|---|---|
| 47 | 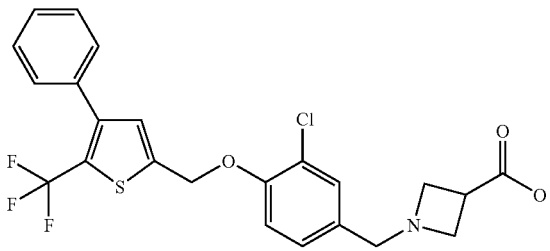 |
| 48 | 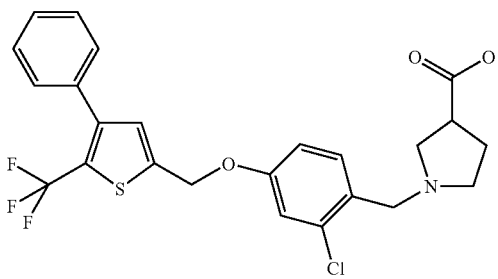 |
| 49 | 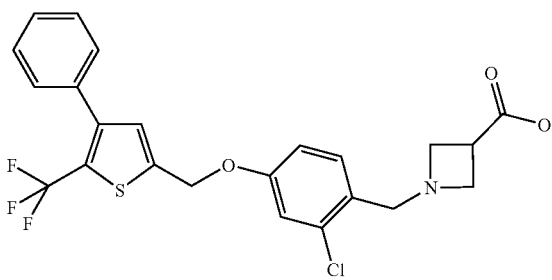 |
| 50 | 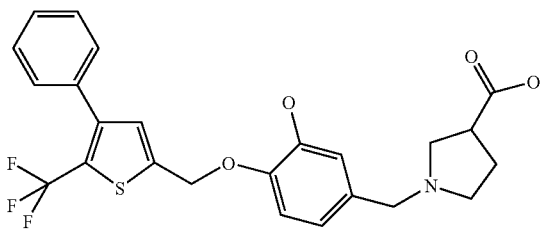 |
| 51 | 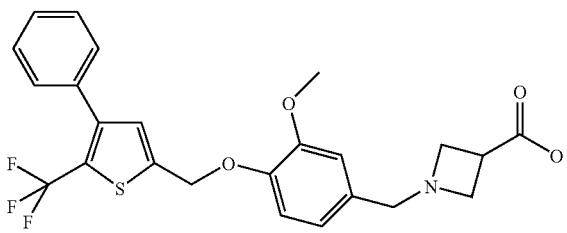 |
| 52 | 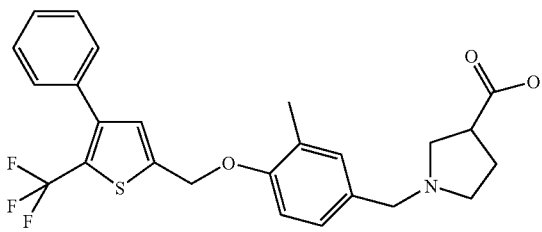 |

-continued
| Example No. | Structure |
|---|---|
| 53 | 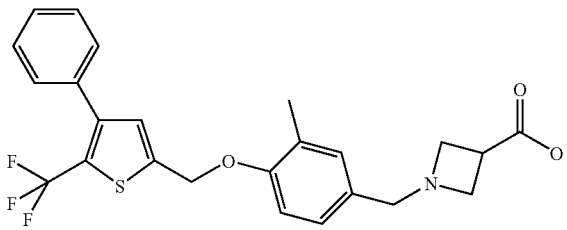 |
| 54 | 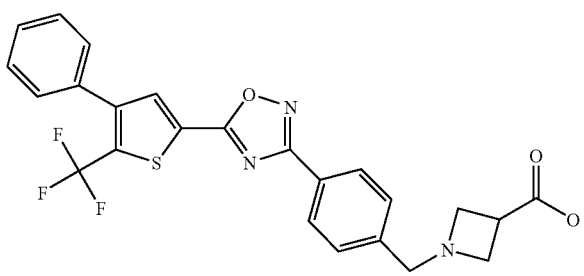 |
| 55 | 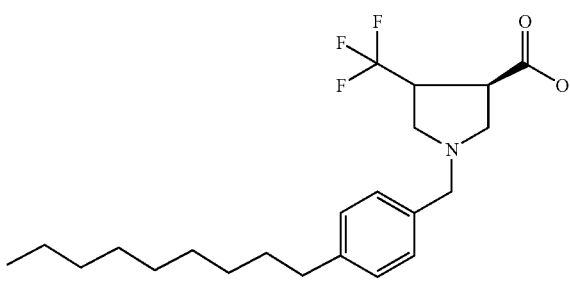 |
| 56 | 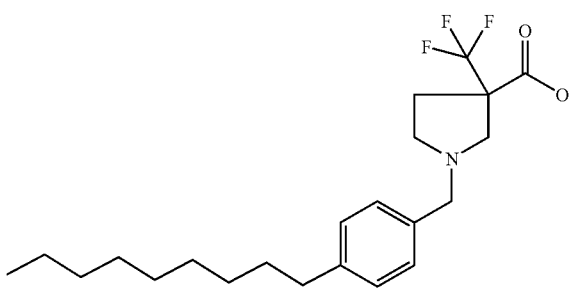 |
| 57 | 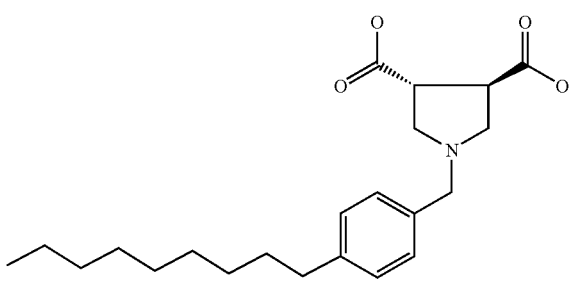 |

| Example No. | Structure |
|---|---|
| 58 | 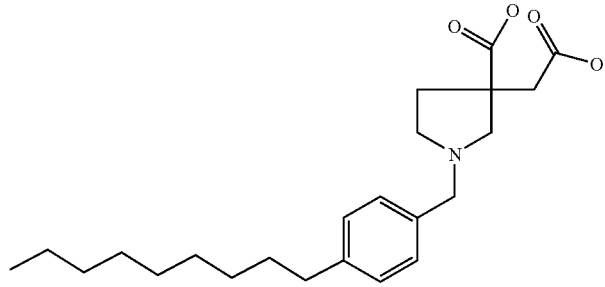 |

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkoxy" means alkoxy groups of a straight, branched or cyclic configuration having the indicated number of carbon atoms. $C_{1-6}$alkoxy, for examples, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes propenyl, 1-methylethenyl, butenyl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aryloxy" means an aryl group as defined above attached to a molecule by an oxygen atom (aryl-O) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by an sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

The term "HET" is defined as a 5- to 10-membered aromatic, partially aromatic or non-aromatic mono- or bicyclic ring, containing 1-5 heteroatoms selected from O, S and N, and optionally substituted with 1-2 oxo groups. Preferably, "HET" is a 5- or 6-membered aromatic or non-aromatic monocyclic ring containing 1-3 heteroatoms selected from O, S and N, for example, pyridine, pyrimidine, pyridazine, furan, thiophene, thiazole, oxazole, isooxazole and the like, or heterocycle is a 9- or 10-membered aromatic or partially aromatic-bicyclic ring containing 1-3 heteroatoms selected from O, S, and N, for example, benzofuran, benzothiophene, indole, pyranopyrrole, benzopyran, quionoline, benzocyclohexyl, naphtyridine and the like. "HET" also includes the following: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl. A preferred group of HET is as follows:

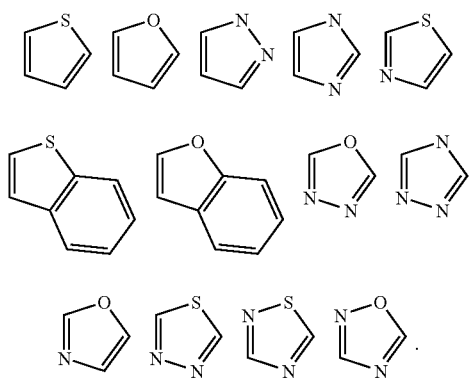

The term "treating" encompasses not only treating a patient to relieve the patient of the signs and symptoms of the disease or condition but also prophylactically treating an asymptomatic patient to prevent the onset or progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The invention described herein includes pharmaceutically acceptable salts and hydrates. Pharmaceutically acceptable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or pamoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

For purposes of this Specification, "pharmaceutically acceptable hydrate" means the compounds of the instant invention crystallized with one or more molecules of water to form a hydrated form.

The invention also includes the compounds falling within formula I in the form of one or more stereoisomers, in substantially pure form or in the form of a mixture of stereoisomers. All such isomers are encompassed within the present invention.

By virtue of their $S1P_1/Edg1$ agonist activity, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also embodied within the present invention is a method of preventing or treating resistance to transplantation or transplantation rejection of organs or tissues in a mammalian patient in need thereof, which comprises administering a therapeutically effective amount of the compound of Formula I.

A method of suppressing the immune system in a mammalian patient in need thereof, which comprises administering to the patient an immune system suppressing amount of the compound of Formula I is yet another embodiment.

Most particularly, the method described herein encompasses a method of treating or preventing bone marrow or organ transplant rejection which is comprised of administering to a mammalian patient in need of such treatment or prevention a compound of formula I, or a pharmaceutically acceptable salt or hydrate thereof, in an amount that is effective for treating or preventing bone marrow or organ transplant rejection.

Furthermore, a preferred group of compounds of the present invention are agonists of the $S1P_1$/Edg1 receptor having selectivity over $S1P_3$/Edg3 receptor. An Edg1 selective agonist has advantages over current therapies and extends the therapeutic window of lymphocytes sequestration agents, allowing better tolerability with higher dosing and thus improving efficacy as monotherapy. The following compounds possesses a selectivity for the $S1P_1$/Edg1 receptor over the $S1PR_3$/Edg3 receptor of at least 20 fold as measured by the ratio of $EC_{50}$ for the $S1P_1$/Edg1 receptor to the $EC_{50}$ for the $S1P_3$/Edg3 receptor as evaluated in the $^{35}$S-GTPγS binding assay and possesses an $EC_{50}$ for binding to the $S1P_1$/Edg1 receptor of 100 nM or less as evaluated by the $^{35}$S-GTPγS binding assay:

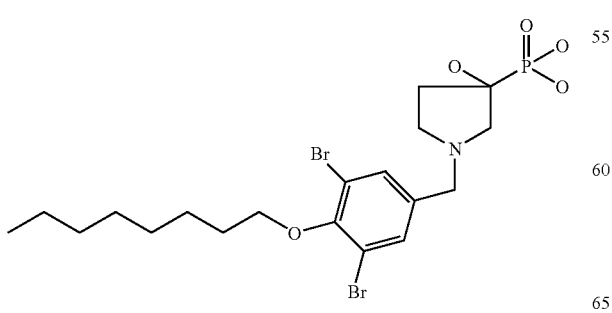

-continued

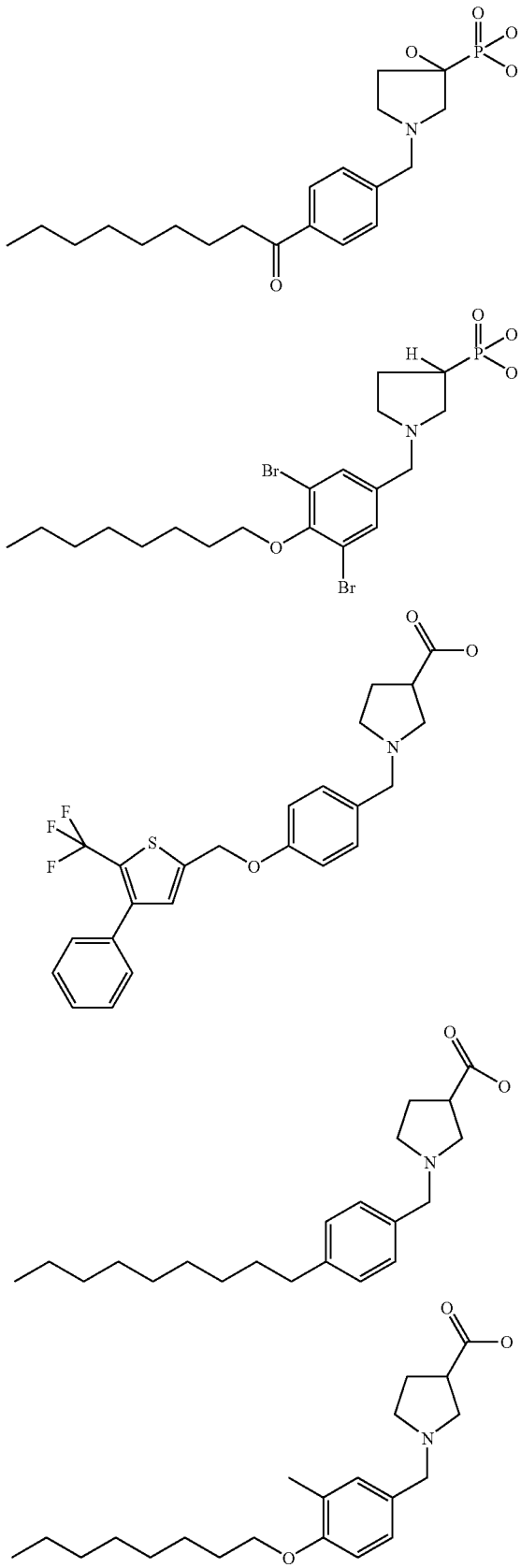

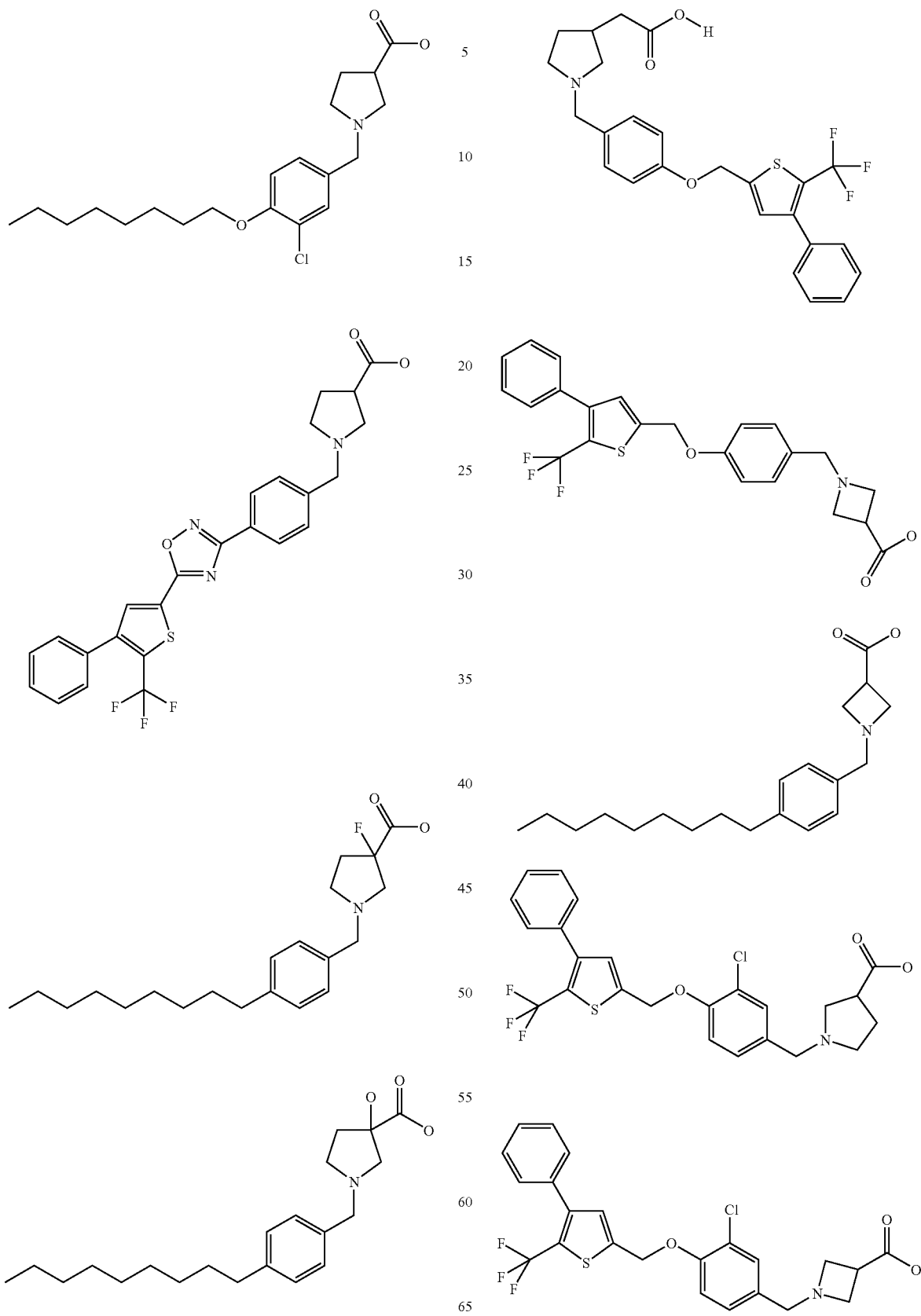

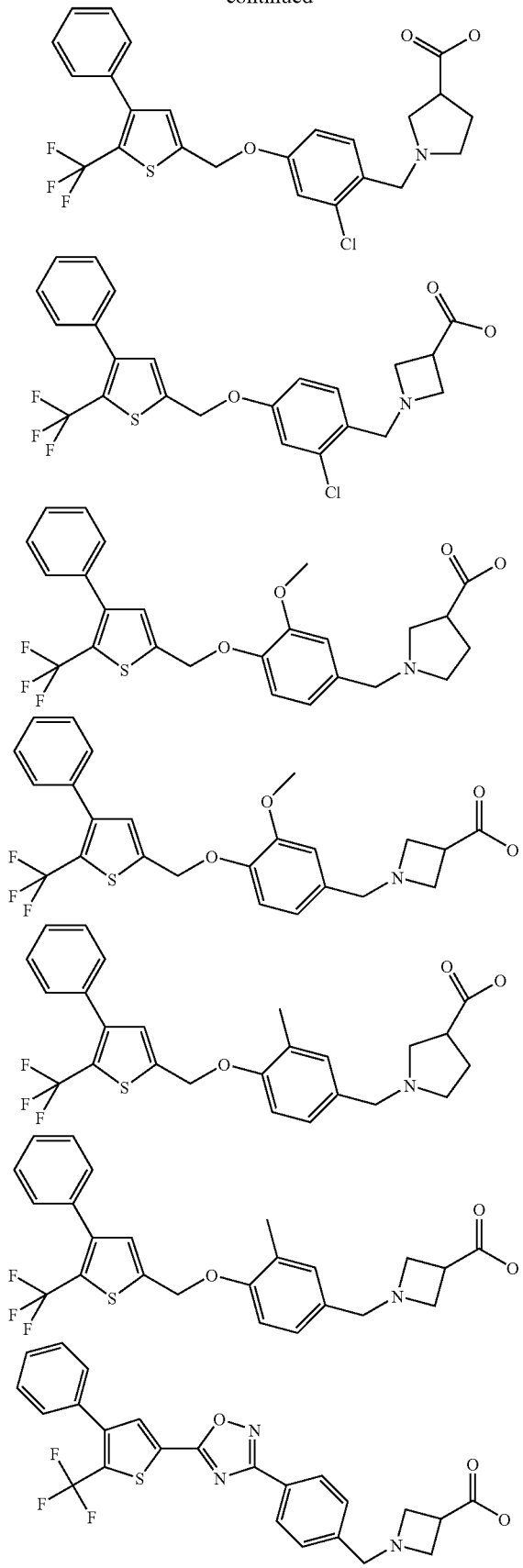

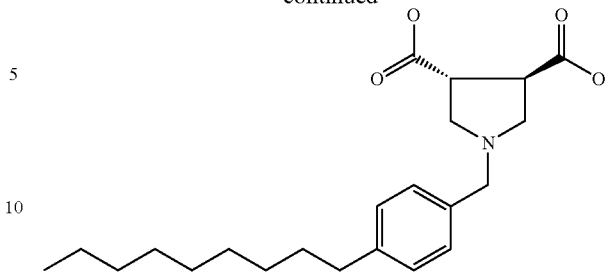

The present invention also includes a pharmaceutical formulation comprising a pharmaceutically acceptable carrier and the compound of Formula I or a pharmaceutically acceptable salt or hydrate thereof. A preferred embodiment of the formulation is one where a second immunosuppressive agent is also included. Examples of such second immunosuppressive agents are, but are not limited to azathioprine, brequinar sodium, deoxyspergualin, mizaribine, mycophenolic acid morpholino ester, cyclosporin, FK-506, rapamycin and FTY720.

The present compounds, including salts and hydrates thereof, are useful in the treatment of autoimmune diseases, including the prevention of rejection of bone marrow transplant, foreign organ transplants and/or related afflictions, diseases and illnesses.

The compounds of this invention can be administered by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 1 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Methods of Synthesis

Two general methods that can be employed to prepare compounds in the current invention are depicted in Scheme 1. Intermediates i may be available from commercial sources (e.g., azetidine-3-carboxylic acid, where $R_1$=H, $R_2$=H, m=0, n=0 or pyrrolidine-3-carboxylic acid, where $R_1$=H, $R_2$=H, m=0, n=1) or they can be prepared using methods described below. Combining i with an aryl aldehyde ii in the presence of an appropriate reducing agent (e.g., sodium cyanoborohydride, sodium triacetoxyborohydride, sodium borohydride) in a compatible solvent (e.g., methanol, ethanol, acetonitrile, methylene chloride) can afford compounds of structure iii. Alternatively, intermediates i can be combined with a benzyl halide or sulfonate ester iv in the presence of an appropriate base (e.g., sodium carbonate, potassium carbonate, triethylamine, N,N-diisopropylethylamine) in a compatible solvent solvent (e.g., methanol, ethanol, acetonitrile) at or above room temperature to give compounds of structure iii. In cases where A in structure i would interfere with the transformation to iii, an appropriate protecting group (Greene & Wuts, eds., "Protecting Groups in Organic Synthesis", John Wiley & Sons, Inc.) that would mask A and allow for the liberation of A after coupling with either ii or iv can be employed. In cases where iii contains asymmetric centers, the individual stereoisomers of iii can obtained by methods known to those skilled in the art which include (but are not limited to): stereospecific synthesis, resolution of salts of iii or any of the intermediates used in its preparation with enantiopure acids or bases, resolution of iii or any of the intermediates used in its preparation by HPLC employing enantiopure stationary phases.

Compounds in the current invention in which m=0, n=1 and A=—CO$_2$H can be prepared using methods shown in Scheme 2. An acrylic acid (v) substituted with functional groups R$_1$ and/or R$_2$ (e.g., R$_1$ and/or R$_2$=H, alkyl, trihaloalkyl or carboxy) can be reacted with an azomethine ylide generated from vi in the presence of a catalytic amount of an acid (e.g., trifluoroacetic acid, phosphoric acid) in an appropriate solvent (e.g., methylene chloride, acetonitrile) to give compounds of the structure vii. Alternatively, viii (prepared similarly to vii, but employing an acrylate ester as the starting material) can be treated with a strong base (e.g., lithium diisopropylamide, sodium bis(trimethylsilyl)amide, potassium bis(trimethylsilyl)amide) in an ethereal solvent (e.g., THF, 1,2-dimethoxyethane) at or below room temperature followed by an electrophile (e.g., methyl iodide, 2-(phenylsulfonyl)-3-phenyloxaziridine, fluorobenzenesulfonimide) to give ix. Saponification of ix can then give vii. In cases

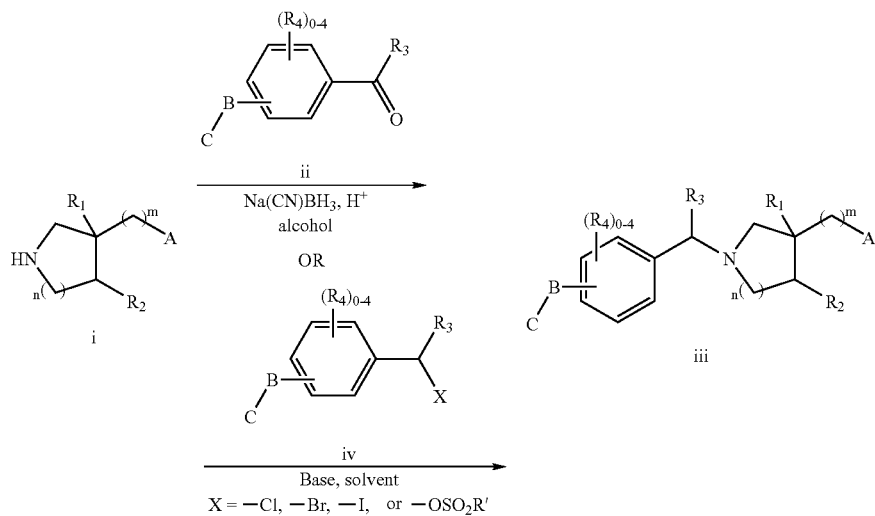

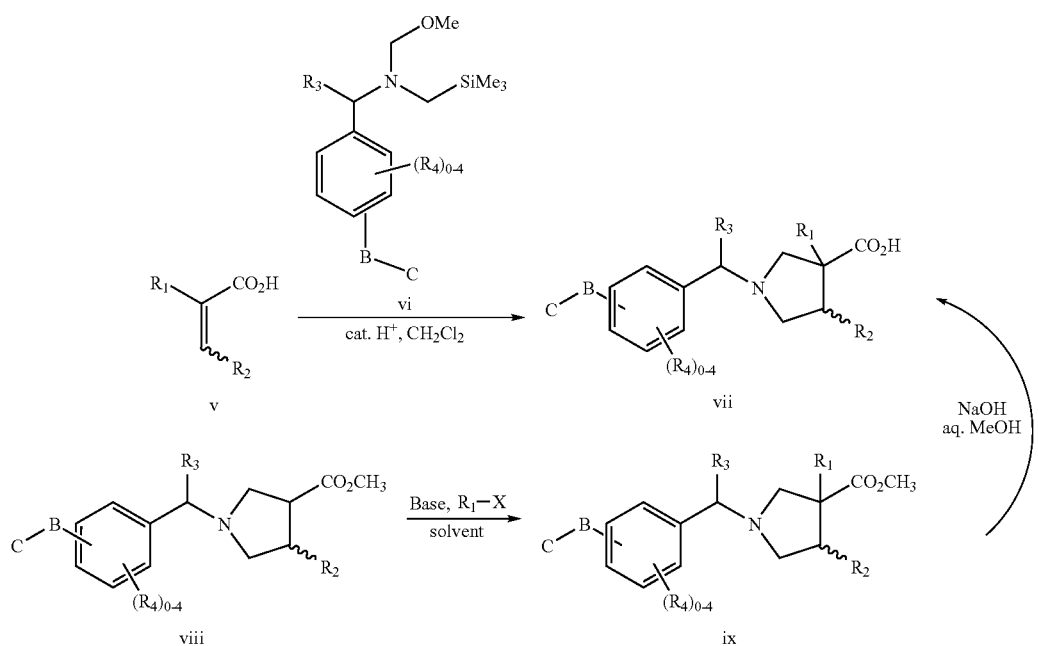

where vii contains asymmetric centers, individual stereoisomers can be obtained using methods similar to those described for iii in Scheme 1.

Several methods that can be used to prepare compounds that could be employed as intermediate i in Scheme 1 above are shown in Scheme 3. For cases where m=0, n=1, $R_1$=H, $R_2$=H and A=—$PO_3H_2$, diethyl vinylphosphonate (x) can be reacted with N-methoxymethyl-N-trimethylsilylmethyl benzyl amine in in the presence of a catalytic amount of an acid (e.g., trifluoroacetic acid, phosphoric acid) in an appropriate solvent (e.g., methylene chloride, acetonitrile) to a give compound of the structure xi. Cleavage of the N-benzyl group using catalytic hydrogenation ($H_2$, Pd(OH)$_2$/C, HOAc; ammonium formate, Pd(OH)$_2$/C, MeOH) or chemical methods (1-chloroethyl chloroformate, DCE, reflux, followed by MeOH, reflux) can give xii. For cases where m=0, n=1, $R_1$=OH, $R_2$=H and A=—$PO_3H_2$, N-t-butoxycarbonyl protection of 3-hydroxypyrrolidine (xiii) followed by mild oxidation (e.g., treatment with oxalyl chloride and DMSO at −78° C. in dichloromethane followed by a trialkylamine base and warming (Swern oxidation); treatment with 4-methylmorpholine N-oxide and catalytic tetrapropylammonium peruthenate in acetonitrile) can give xiv. Treating xiv with a dialkylphosphite in the presence of a tertiary amine base (triethylamine, N,N-diisopropylethylamine) at or above room temperature followed by removal of the t-butylcarbamate under acidic conditions (e.g., HCl in MeOH, neat TFA) can give xv. For cases where m=0, n=1, $R_1$=H, $R_2$=H and A=5-tetrazolyl, acrylonitrile (xvi) can be reacted with N-methoxymethyl-N-trisilylmethyl benzyl amine in the presence of a catalytic amount of an acid (e.g., trifluoroacetic acid, phosphoric acid) in an appropriate solvent (e.g., methylene chloride, acetonitrile) to a give compound of the structure xvii. Converting the N-benzyl group of xvii to a benzyl carbamate following by tetrazole formation (e.g., ammonium chloride, sodium azide, DMF at elevated temperature; trimethyltin azide, toluene, reflux) then catalytic hydrogenation can give xviii.

Several methods that can be used to prepare compounds that can be employed as intermediate ii in Scheme 1 above are shown in Scheme 4. Many aryl carboxylic acids, aryl carboxylic acid halides, aryl carboxylic esters, and aryl N-alkoxyl-N-alkyl carboxamides (xix) are commercially available and can be converted to aryl aldehydes (xx) using reduction methods known by those skilled in the art (see Larock, "Comprehensive Organic Transformations, A Guide to Functional Group Preparations", VCH Publishers, Inc.). Alternatively, many benzyl alcohols (xxi) are commercially Scheme 3

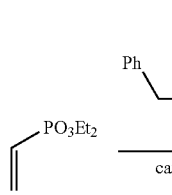

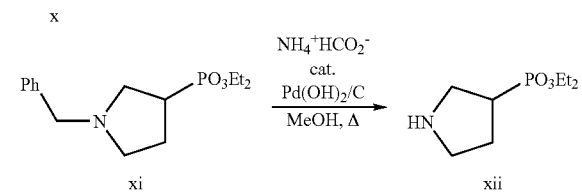

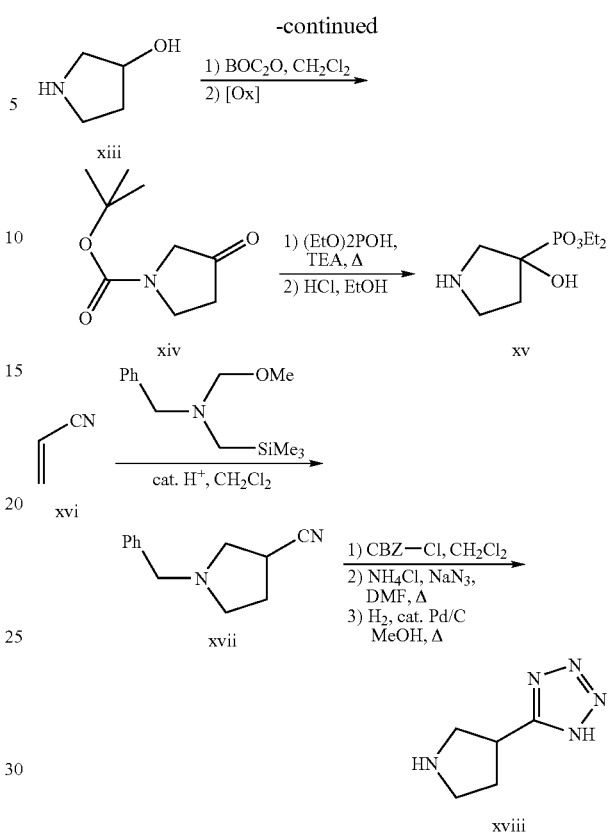

available and can be converted to aryl aldehydes (xxii) using oxidation methods known by those skilled in the art. For cases where B=alkoxy, a hydroxy benzaldehyde xxi can be combined with a alkyl halide or sulfonate ester in the presence of an appropriate base (e.g., sodium carbonate, potassium carbonate, triethylamine, N,N-diisopropylethylamine) in a compatible solvent solvent (e.g., methanol, ethanol, acetonitrile) at or above room temperature to give compounds of structure xxiv. Alternatively, a hydroxy benzaldehyde xxiii can be combined with an alcohol, a dialkyl azodicarboxylate (e.g., diethyl azodicarboxylate, diisopropylazodicarboxylate) and triphenylphosphine in an appropriate solvent (THF, toluene, methylene chloride) to give xxiv. For cases where B is 1,2,4-oxadiazolyl, N-hydroxyamidine xxv can be treated with an acid chloride in an appropriate solvent (xylenes, toluene) in the presence of an amine base (pyridine, DBU) with heating to give an intermediate xxvi. Alternatively, xxv can be treated with a carboxylic acid, a carbodiimide (e.g., N,N'-dicyclohexylcarbodiimide, 1-[3-(dimethylamino)propyl]-3-ethylcarbodiimide) and 1-hydroxybenzotriazole in an appropriate solvent (xylenes, toluene) to give xxvi. Prepared by either manner, the ester group of xxvi can be converted to aldehyde with methods employed to convert xix to xx. For cases where B is —(C═O)$C_{6-11}$ alkyl and $R_4$=H, an aryl 1,4-dialdehyde (xxvii) can be treated with a limiting amount of an alkyl organometallic reagent (e.g., alkyl magnesium bromide, alkyl lithium) at or below room temperature in an ethereal solvent (e.g., THF, diethyl ether, 1,2-dimethoxyethane) to afford intermediate xxviii. Mild oxidation of xxviii (e.g., treatment with oxalyl chloride and DMSO at −78° C. in dichloromethane followed by a trialkylamine base and warming (Swern oxidation); treatment with 4-methylmorpholine N-oxide and catalytic tetrapropylammonium peruthenate in acetonitrile) can give aldehyde xix.

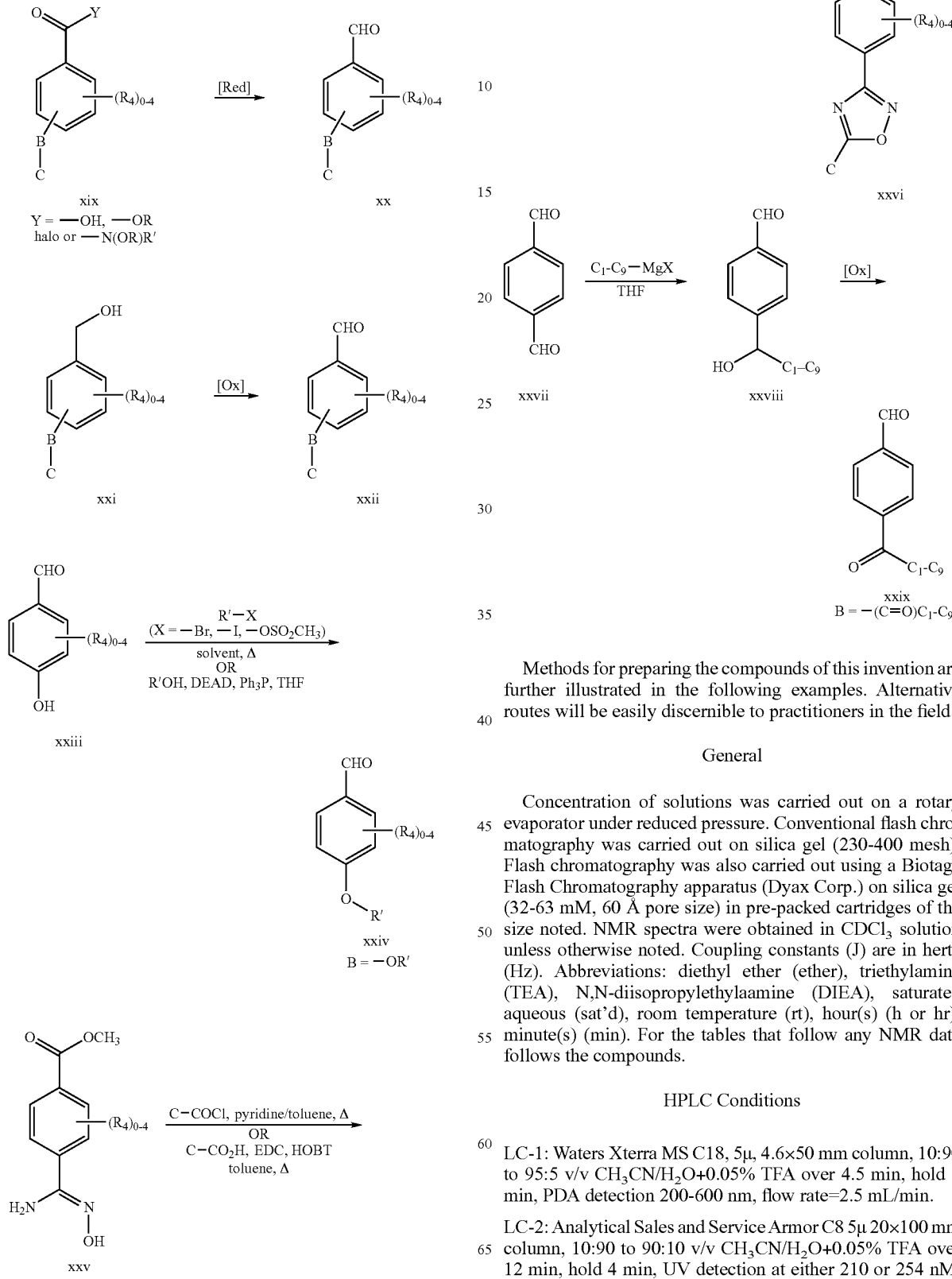

Methods for preparing the compounds of this invention are further illustrated in the following examples. Alternative routes will be easily discernible to practitioners in the field.

General

Concentration of solutions was carried out on a rotary evaporator under reduced pressure. Conventional flash chromatography was carried out on silica gel (230-400 mesh). Flash chromatography was also carried out using a Biotage Flash Chromatography apparatus (Dyax Corp.) on silica gel (32-63 mM, 60 Å pore size) in pre-packed cartridges of the size noted. NMR spectra were obtained in $CDCl_3$ solution unless otherwise noted. Coupling constants (J) are in hertz (Hz). Abbreviations: diethyl ether (ether), triethylamine (TEA), N,N-diisopropylethylaamine (DIEA), saturated aqueous (sat'd), room temperature (rt), hour(s) (h or hr), minute(s) (min). For the tables that follow any NMR data follows the compounds.

HPLC Conditions

LC-1: Waters Xterra MS C18, 5μ, 4.6×50 mm column, 10:90 to 95:5 v/v $CH_3CN/H_2O$+0.05% TFA over 4.5 min, hold 1 min, PDA detection 200-600 nm, flow rate=2.5 mL/min.

LC-2: Analytical Sales and Service Armor C8 5μ 20×100 mm column, 10:90 to 90:10 v/v $CH_3CN/H_2O$+0.05% TFA over 12 min, hold 4 min, UV detection at either 210 or 254 nM, flow rate=10 mL/min.

Preparation of Aldehyde Intermediates

Aldehyde 1

4-Nonylbenzaldehyde

A solution of 2.0 g (7.5 mmol) of 4-nonylbenzoyl chloride in 75 mL of THF at −78° C. was treated with 7.5 mL (7.5 mmol) of 1M lithium tri-(tert-butoxy) aluminum hydride in THF. After 30 min at −78° C., the reaction was quenched with 2N HCl and was allowed to warm to rt. The mixture was poured into $Et_2O$ and washed with 2N HCl, sat'd $NaHCO_3$ and sat'd NaCl. The organic layer was dried over $MgSO_4$ and concentrated. The residue was purified on a 40M Biotage column using 100:1 v/v hexane/$Et_2O$ as the eluant to afford 708 mg (41%) of the title compound: $^1$H-NMR (500 MHz) δ 0.87 (t, J=7.0, 3H), 1.26-1.31 (m, 12H), 1.60-1.66 (m, 2H), 2.68 (t, J=7.8, 2H), 7.32 (d, J=8.0, 2H), 7.79 (d, J=8.0, 2H), 9.97 (s, 1H).

Aldehyde 2

4-Decylbenzaldehyde

The title compound was prepared using a procedure analogous to Aldehyde 1 substituting 4-decylbenzoyl chloride for 4-nonylbenzoyl chloride: $^1$H-NMR (500 MHz) δ 0.87 (t, J=6.9, 3H, 1.25-1.31 (m, 14H), 1.60-1.66 (m, 2), 2.68 (t, J=7.7, 2H), 7.33 (d, J=8.0, 2H), 7.79 (d, J=8.0, 2H), 9.97 (s, 1H).

Aldehyde 3

3-(Octyloxy)benzaldehyde

A mixture of 1.00 g (0.82 mmol) of 3-hydroxybenzaldehyde, 1.70 g (12.2 mmol) of potassium carbonate and 2.16 g (9.00 mmol) of 1-iodooctane were warmed in acetonitrile at 80° C. for 16 h. The reaction was cooled, filtered and concentrated. The residue was purified using flash chromatography using 20:1 v/v hexane/ethyl acetate to afford 1.63 g of the title compound as a colorless oil: $^1$H-NMR (500 MHz) δ 0.89 (t, J=6.9, 3H), 1.24-1.39 (m, 8H), 1.42-1.50 (m, 2H), 1.80 (m, 2H), 4.01 (t, J=6.6, 2H), 7.19 (m, 1H), 7.40 (s, 1H), 7.44-7.46 (m, 2H), 9.99 (s, 1H).

Aldehyde 4

4-(Octyloxy)benzaldehyde

The title compound was prepared using a procedure analogous to Aldehyde 3 substituting 4-hydroxybenzaldehyde for 3-hydroxybenzaldehyde: $^1$H NMR (500 MHz) δ 0.91 (t, J=6.9, 3H), 1.29-1.41 (m, 8H), 1.46-1.52 (m, 2H), 1.71-1.86 (m, 2H), 4.06 (t, J=6.6, 2H), 7.01 (d, J=8.7, 2H), 7.85 (d, J=8.7, 2H), 9.90 (s, 1H).

Aldehyde 5

3-Bromo-5-methoxy-4-octyloxybenzaldehyde

The title compound was prepared using a procedure analogous to Aldehyde 3 substituting 3-bromo-4-hydroxy-5-methoxybenzaldehyde for 3-hydroxybenzaldehyde: ESI-MS: 343 (M+H)

Aldehyde 6

3-Ethoxy-4-(octyloxy)benzaldehyde

The title compound was prepared using a procedure analogous to Aldehyde 3 substituting 3-ethoxy-4-hydroxybenzaldehyde for 3-hydroxybenzaldehyde: $^1$H-NMR (500 MHz) δ 0.88-0.98 (m, 3H), 1.30-1.41 (m, 8H), 1.46-1.51 (m, 5H), 1.85-1.91 (m, 2H), 4.06-4.18 (m, 4H), 6.97 (d, J=8.0, 1H), 7.39-7.44 (m, 2H), 9.84 (s, 1H); ESI-MS 279.1 (M+H).

Aldehyde 7

3,5-Dibromo-4-(octyloxy)benzaldehyde

The title compound was prepared using a procedure analogous to Aldehyde 3 substituting 3,5-dibromo-4-hydroxybenzaldehyde for 3-hydroxybenzaldehyde.

Aldehyde 8

3-Methoxy-4-(octyloxy)benzaldehyde

The title compound was prepared using a procedure analogous to Aldehyde 3 substituting 3-methoxy-4-hydroxybenzaldehyde for 3-hydroxybenzaldehyde: ESI-MS 265.2 (M+H)

Aldehyde 9

3-Methyl-4-(octyloxy)benzaldehyde

The title compound was prepared using a procedure analogous to Aldehyde 3 substituting 3-methyl-4-hydroxybenzaldehyde for 3-hydroxybenzaldehyde.

Aldehyde 10

4-(Octyloxy)-1-naphthaldehyde

The title compound was prepared using a procedure analogous to Aldehyde 3 substituting 4-hydroxy-1-naphthaldehyde for 3-hydroxybenzaldehyde.

Aldehyde 11

2-Chloro-4-(octyloxy)benzaldehyde

The title compound was prepared using a procedure analogous to Aldehyde 3 substituting 2-chloro-4-hydroxybenzaldehyde for 3-hydroxybenzaldehyde: ESI-MS 269.0 (M+H)

Aldehyde 12

3-Chloro-4-(octyloxy)benzaldehyde

The title compound was prepared using a procedure analogous to Aldehyde 3 substituting 3-chloro-4-hydroxybenzaldehyde for 3-hydroxybenzaldehyde.

Aldehyde 13

4-(trans-3,7-Dimethyl-2,6-octadien-1-yloxy)benzaldehyde

The title compound was prepared using a procedure analogous to Aldehyde 3 using 4-hydroxybenzaldehyde and geranyl bromide: $R_F$: 0.29 (19:1 v/v hexane/EtOAc); $^1$H-NMR (500 MHz) δ 1.58-1.83 (m, 9H), 2.00-2.16 (m, 4H), 4.65 (d, J=6.6, 2H), 5.10 (m, 1H), 5.50 (m, 1H), 7.02 (d, J=8.7, 2H), 7.85 (d, J=8.7, 2H), 9.90 (s, 1H).

Aldehyde 14

4-[Bis(3,5-trifluoromethyl)benzyloxy]benzaldehyde

The title compound was prepared using a procedure analogous to Aldehyde 3 using 4-hydroxybenzaldehyde and bis(3,5-trifluoromethyl)benzyl bromide: $R_F$: 0.28 (9:1 v/v hexane/EtOAc); $^1$H-NMR (500 MHz) δ 5.28 (s, 2H), 7.14 (d, J=8.7, 2H), 7.91-7.95 (m, 5H), 9.95 (s, 1H).

Aldehyde 15

3-(4-(Formyl)phenyl)-5-(4-phenyl-5-trifluoromethyl-2-thienyl)-1,2,4-oxadiazole Step A: (E/Z)-2-Phenyl-3-chloro-4,4,4-trifluoro-2-butanal Phosphorous oxychloride (7.5 mL, 80 mmol) was added to 15 mL of DMF at 0° C. The resulting mixture was warmed to rt and stirred for 1 h. A solution of 5.0 g (26.6 mmol) of 1,1,1-trifluoromethyl-3-phenyl-2-propanone in 1 mL of DMF was added and the resulting mixture was stirred at 70° C. for 20 h. The reaction mixture was cooled to rt, poured onto 150 g of ice and stirred at ambient temperature for 1 h. The quenched mixture was extracted with 200 mL of ether. The extract was washed with 200 mL of water, dried and concentrated. Chromatography on a Biotage 40 M cartridge using hexanes (4 L) as the eluant afforded 5.1 g (82%) of the title compound.

Step B: Ethyl (4-phenyl-5-trifluoromethyl)thiophene-2-carboxylate

Ethyl mercaptoacetate (2.75 mL, 25.0 mmol) was added to a suspension of 600 mg (25 mmol) of NaH in 45 mL of THF maintaining the internal temperature at 25° C. A solution of 5.10 g (21.7 mmol) of (E/Z)-2-phenyl-3-chloro-4,4,4-trifluoro-2-butanal (from Step A) was added and the resulting mixture was stirred at rt for 20 h. The reaction was quenched with 50 mL of sat'd NH$_4$Cl and the resulting mixture was partitioned between 250 mL of ether and 100 mL of water. The organic layer was separated, dried and concentrated. Chromatography on a Biotage 40 M cartridge using hexanes (1L), then 4:1 v/v hexanes/CH$_2$Cl$_2$ (1 L) as the eluant afforded 5.10 g (78%) of the title compound: $^1$H NMR (400 Mhz) δ 1.40 (t, J=7.2, 3H), 4.39 (q, J=7.2, 2H), 7.42 (app s, 5H), 7.74 (q, J=1.6, 1H).

Step C: (4-Phenyl-5-trifluoromethyl)thiophene-2-carboxylic acid

A solution of 5.10 g (17.0 mmol) of ethyl 4-phenyl-5-trifluoromethyl-thiophene-2-carboxylate (from Step B) in 20 mL of EtOH was treated with 10 mL of 5.0 N NaOH and stirred at rt for 30 min. The EtOH was removed in vacuo. The residual aqueous mixture was acidified to pH 2 with 1 N HCl, then extracted with 300 mL of 1:1 v/v EtOAc/ether. The extract was separated, dried and concentrated. Recrystallization from 200 mL of 20:1 v/v hexanes/ether afforded 4.30 g (93%) of the title compound: $^1$H NMR (500 Mhz) δ 7.43 (app s, 5H), 7.84 (app s, 1H); $^{13}$C NMR (CDCl$_3$, 125 Mhz) δ 121.7 (q, J=269), 128.5, 128.6, 128.8, 132.5 (q, J=36), 133.3, 133.8, 137.5, 144.8, 167.0.

Step D: 3-[4-(Carbomethoxy)phenyl]-5-(4-phenyl-5-trifluoromethyl-2-thienyl)-1,2,4-oxadiazole A solution of 408 mg (1.5 mmol) of 4-phenyl-5-trifluoromethyl-thiophene-2-carboxylic acid and 1 mL of oxalyl chloride in 5 mL of CH$_2$Cl$_2$ was treated with 5 drops of DMF. The resulting mixture was stirred at rt for 1 h, then concentrated. The crude acid chloride and 291 mg (1.5 mmol) of 4-(carbomethoxy)benzamidoxime were dissolved in 7 mL of 6:1 v/v xylenes/pyridine. The resulting solution was heated at 140° C. for 1 h, then cooled. The mixture was partitioned between 50 mL of 1:1 EtOAc/ether and 50 mL of 1 N HCl. The organic layer was separated, washed with 3×50 mL of 1 N HCl, 50 mL of sat'd NaHCO$_3$, dried and concentrated. Chromatography on a Biotage 40 M cartridge using hexanes (1L), then 20:1 v/v hexanes/EtOAc (1 L) as the eluant afforded 423 mg (65%) of the title compound: $^1$H NMR (500 Mhz) δ0 3.97 (s, 3H), 7.48 (app s, 5H), 7.92 (s, 1H), 8.18 (app d, J=8.5, 2H), 8.23 (app d, J=8.5, 2H).

Step E: 3-[4-(Hydroxymethyl)phenyl]-5-(4-phenyl-5-trifluoromethyl-2-thienyl)-1,2,4-oxadiazole A solution of 390 mg (0.91 mmol) of 3-[4-(carbomethoxy)phenyl]-5-(4-phenyl-5-trifluoromethyl-2-thienyl)-1,2,4-oxadiazole (from Step D) in 10 mL of CH$_2$Cl$_2$ at −78° C. was treated with 2.7 mL of 1.0 M DIBALH solution in CH$_2$Cl$_2$. The resulting solution was stirred cold for 1 h, then quenched with 5 mL of sat'd Rochelle salt solution. The mixture was partitioned between 100 mL CH$_2$Cl$_2$ and 50 mL of 1 N NaOH. The organic layer was separated, dried and concentrated. Chromatography on a Biotage 40 S cartridge using 4:1 v/v hexanes/EtOAc (1L) as the eluant afforded 325 mg (89%) of the title compound: $^1$H NMR (500 Mhz) δ 1.80 (app s, 1H), 4.80 (d, J=4.0, 2H), 7.46-7.48 (5H), 7.52 (d, J=8.0, 2H), 7.91 (q, J=1.5, 1H), 8.14 (d, J=8.0, 2H).

Step P: 3-[4-(Formyl)phenyl]-5-(4-phenyl-5-trifluoromethyl-2-thienyl)-1,2,4-oxadiazole A mixture of 310 mg (0.77 mmol) of 3-[4-(hydroxymethyl)phenyl]-5-(4-phenyl-5-trifluoromethyl-2-thienyl)-1,2,4-oxadiazole (from Step E), 527 mg (1.5 mmol) of 4-methylmorpholine N-oxide and 500 mg of 4 A molecular sieves in 15 mL of CH$_3$CN was treated with 12 mg (0.034 mmol) of tetrapropylammonium perruthnate and the resulting mixture was stirred ar rt for 2 h. The solids were filtered and the filtrated was concentrated. Chromatography on a Biotage 40 S cartridge using 9:1 v/v hexanes/EtOAc (1L) as the eluant afforded 205 mg (66%) of the title compound: $^1$H NMR (500 Mhz) δ 7.48 (app s, 5H), 7.93 (app s, 1H), 8.03 (d, J=8.5, 2H), 8.33 (d, J=8.5, 2H), 10.1 (s, 1H).

Aldehyde 16

4-[(4-Phenyl-5-trifluoromethyl-2-thienyl)methoxy]benzaldehyde

Step A: 2-Hydroxymethyl-4-phenyl-5-trifluoromethylthiophene

A solution of 2.10 g (7.7 mmol) of 4-phenyl-5-trifluoromethyl-thiophene-2-carboxylic acid (from Aldehyde 15, Step C) in 20 mL of THF was treated with 5.0 mL of 2.0 M borane dimethylsulfide complex in THF. The resulting solution was heated at reflux for 3 h, cooled to rt, quenched with 10 mL of MeOH and concentrated. Chromatography on a Biotage 40M cartridge using 9:1 v/v hexanes/EtOAc as the eluant afforded 1.95 g (98%) of the title compound: $^1$H NMR (500 Mhz) δ 2.05 (app s, 1H), 4.87 (s, 2H), 6.99 (s, 1H), 7.41 (app s, 5H).

Step B: 4-((4-Phenyl-5-trifluoromethyl-2-thienyl)methoxy) benzaldehyde

A solution of 1.95 g (7.5 mmol) of 2-hydroxymethyl-4-phenyl-5-trifluoromethyl-thiophene (from Step A), 925 mg (7.6 mmol) of 4-hydroxybenzaldehyde and 3.0 g (11.4 mmol) of triphenylphosphene in 40 mL of THF at 0° C. was treated with 2.0 g (11.4 mmol) of diethylazodicarboxylate. The resulting mixture was warmed to rt, stirred for 2 h, then concentrated. Chromatography on a Biotage 75S cartridge using 9:1 v/v heptane/EtOAc as the eluant afforded 2.5 g of impure title compound. Chromatography on a Biotage 40M cartridge using 19:1 v/v hexanes/EtOAc (1L), then 4:1 v/v hexanes/EtOAc (1L) as the eluant afforded 1.65 g (60%) of the title compound: $^1$H NMR (500 Mhz) δ 5.32 (s, 2H), 7.10 (d, J=8.5, 2H), 7.12 (s, 1H), 7.41-7.43 (5H), 7.85-7.90 (2H), 9.92 (s, 1H).

Aldehydes 17-21 were prepared using procedures analogous to those described in Aldehyde 16 substituting the appropriately substituted benzaldehyde for 4-(hydroxy)benzaldehyde in Step B:

Aldehyde 17

3-((4-Phenyl-5-trifluoromethyl-2-thienyl)methoxy)benzaldehyde

Aldehyde 18

2-Chloro-4-((4-phenyl-5-trifluoromethyl-2-thienyl)methoxy)benzaldehyde

Aldehyde 19

3-Chloro-4-((4-phenyl-5-trifluoromethyl-2-thienyl)methoxy)benzaldehyde

Aldehyde 20

3-Methyl-4-((4-phenyl-5-trifluoromethyl-2-thienyl)methoxy)benzaldehyde

Aldehyde 21

3-Methoxy-4-((4-phenyl-5-trifluoromethyl-2-thienyl)methoxy)benzaldehyde

Aldehyde 22

4-(4-Phenylbutoxy)benzaldehyde

The title compound was prepared using a procedure analogous to Aldehyde 4 substituting 4-(iodobutyl)benzene for 1-iodooctane: ESI-MS 255.2 (M+H)

Aldehyde 23

4-(Non-1-oyl)benzaldehyde

Step A: 4-(1-Hydroxynon-1-yl)benzaldehyde

Terephthaldicarboxaldehyde (2.00 g, 14.91 mmol) was dissolved in tetrahydrofuran (25 ml) and cooled to 0° C. Octylmagnesium chloride (7.5 ml, 2.0M in THF, 15 mmol) was added dropwise. After 15 minutes, the reaction was quenched with 2N aqueous hydrochloric acid (50 ml) and diluted with ethyl acetate (50 ml). The organic layer was separated, washed with sat'd NaCl (50 ml), dried over magnesium sulfate and concentrated. Silica gel chromatography eluting with 91:9 v/v hexane/EtOAc gave 0.19 g (0.77 mmol, 5.1%) of the title compound: $^1$H NMR (500 MHz) δ 10.0 (s, 1H), 7.87 (d, J=8.0, 2H), 7.52 (d, J=8.3, 2H), 4.75-4.80 (m, 1H), 1.68-1.82 (m, 2H), 1.22-1.45 (m, 12H), 0.91 (t, J=7.0, 3H).

Step B: 4-(Non-1-oyl)benzaldehyde

Dess-Martin periodinane (0.268 g, 0.632 mmol) was added to a solution of 4-(1-hydroxynon-1-yl)benzaldehyde (0.125 g, 0.505 mmol) from Step A in $CH_2Cl_2$ (3.0 ml). After 1 h, the reaction was filtered and concentrated. Silica gel chromatography eluting with 19:1 v/v hexane/EtOAc gave 0.107 g (0.446 mmol, 88%) of the title compound: $^1$H NMR (500 MHz) δ 10.1 (s, 1H), 8.10 (d, J=8.2, 2H), 7.97 (d, J=8.2, 2H), 3.00 (t, J=7.3, 2H), 1.70-1.8 (m, 2H), 1.22-1.42 (m, 10H), 0.88 (t, J=7.0, 3H).

Aldehyde 24

Heptyl 4-(formyl)benzoate

The title compound was prepared through a condensation between 1-heptanol and 4-formylbenzoic acid. $^1$H NMR (500 MHz, CDCl$_3$): δ 10.10 (s, 1H), 8.20 (d, J=8.2, 2H), 7.95 (d, J=8.2, 2H), 4.35 (t, J=6.8, 2H), 1.75-1.85 (m, 2H), 1.40-1.50 (m, 2H), 1.25-1.40 (m, 6H), 0.89 (t, J=7.0, 3H).

Aldehydes 25 and 26 were prepared using procedures analogous to those described in Aldehyde 16 substituting the appropriately substituted alcohol for 2-hydroxymethyl-4-phenyl-5-trifluoromethyl-thiophene in Step B:

Aldehyde 25

4-[(Benzothien-2-yl)methoxy]benzaldehyde $^1$H NMR (500 MHz) δ 5.34 (s, 2H), 7.04 (d, J=8.7, 2H), 7.18 (s, 1H), 7.25-7.30 (m, 4H), 7.76 (d, J=8.7, 2H), 9.82 (s, 1H).

Aldehyde 26

4-[(2,3-Diphenyl-2H-pyrazol-5-yl)methoxy]benzaldehyde $^1$H NMR (500 MHz) δ 5.21 (s, 2H), 6.55 (s, 1H), 7.10 (d, J=8.7, 2H), 7.14-7.17 (m, 5H), 7.21-7.30 (m, 5H), 7.79 (d, J=8.7, 2H), 9.82 (s, 1H).

PREPARATION OF EXAMPLES

Example 1

(R/S)-1-(4-(Nonyl)phenyl)methyl-3-hydroxy-pyrrolidin-3-yl)phosphonic acid

Step A: (R/S)-1-tert-Butoxycarbonyl-3-hydroxypyrrolidine

A solution of 2.5 g (28.7 mmol) of (R/S)-3-hydroxypyrrolidine in 10 mL of $CH_2Cl_2$ at 0° C. was treated with 6.89 g (31.6 mmol) of di-tert-butyl-dicarbonate in 2 mL $CH_2Cl_2$ and 0.35 g (2.8 mmol) of 4-(N,N-dimethylamino) pyridine. After stirring for 10 min, the reaction was warmed to rt and stirred overnight. The reaction was diluted with 100 mL of $CH_2Cl_2$ and washed with 100 mL of 1N HCl and 100 mL of 1N NaHCO$_3$. The organic layer was dried over Na$_2$SO$_4$ and concentrated. The residue was purified on a 40M Biotage column using 7:3 v/v hexane/acetone as the eluant to afford 5.3 g (99%) of the title compound: R$_F$: 0.26 (7:3 v/v hexane/acetone); $^1$H-NMR (500 MHz) δ 1.45 (s, 9H), 1.88-2.00 (m, 2H), 2.52 (br s, 1H), 3.29-3.50 (m, 4H), 4.42 (m, 1H).

Step B: 1-tert-Butoxycarbonyl-3-oxo-pyrrolidine

A solution of 2.3 mL (26 mmol) of oxalyl chloride in 80 mL of $CH_2Cl_2$ at −78° C. was treated with 3.8 mL (53 mmol) of DMSO in 5 mL of $CH_2Cl_2$. The resulting mixture was stirred cold for 5 min. A solution of 2.0 g (10.7 mmol) of (R/S)-1- tert-butoxycarbonyl-3-hydroxypyrrolidine (from Step A) in 10 mL of $CH_2Cl_2$ was added. The resulting mixture was stirred for 30 min, treated with 18.7 mL (107 mmol) of DIEA and warmed to 0° C. After stirring for 45 min, the reaction was quenched with $H_2O$ and poured into 100 mL of 1N HCl. After separating the layers, the organic layer was washed with 100 mL sat'd NaCl, dried over $Na_2SO_4$ and concentrated. The residue was purified on a 40M Biotage column using 4:1 v/v hexane/acetone as the eluant to afford 1.9 g (96%) of the title compound: $R_F$: 0.49 (7:3 v/v hexane/acetone); $^1$H-NMR (500 MHz) δ 1.48 (s, 9H), 2.58 (t, J=7.9, 2H), 3.71-3.78 (m, 4H).

Step C: (R/S)-1-tert-Butoxycarbonyl-3-hydroxy-pyrrolidin-3-yl phosphonic acid, diethyl ester A mixture of 1.9 g (10.3 mmol) of 1-tert-butoxycarbonyl-3-oxopyrrolidine (from Step B), 1.3 mL (10.3 mmol) of diethyl phosphite and 1.4 mL (10.3 mmol) of TEA was stirred at 100° C. for 1.5 h. Volatiles were removed under reduced pressure. The residue was purified on a 40M Biotage column using 13:7 v/v hexane/acetone as the eluant to afford 1.78 g (53%) of the title compound as a yellow oil: $R_F$: 0.16 (7:3 v/v hexane/acetone); $^1$H-NMR (500 MHz) δ 1.33 (t, J=7.0, 6H), 1.45 (s, 9H), 2.08 (m, 1H), 2.18 (m, 1H), 3.47-3.64 (m, 4H), 4.13-4.22 (m, 4H).

Step D: (R/S)-3-Hydroxy-pyrrolidin-3-yl phosphonic acid, diethyl ester

A solution of 1.78 g (5.5 mmol) of (R/S)-1-tert-butoxycarbonyl-3-hydroxy-pyrrolidin-3-yl phosphonic acid, diethyl ester (from Step C) in 2N HCl in EtOH was stirred at rt for 5.5 h. The reaction was concentrated from $CH_2Cl_2$ several times. The crude product was partitioned between aqueous $NH_4OH$ and $CHCl_3$/isopropanol (3:1 v/v). After separating phases, the aqueous layer was extracted with 3× $CHCl_3$/isopropanol (3:1 v/v). The combined organics were dried over $Na_2SO_4$ and concentrated. The residue was purified on a 40S Biotage column using 90:10:1 v/v/v $CH_2Cl_2$/MeOH/$NH_4OH$ as the eluant to afford the title compound as a light brown oil: $^1$H-NMR (500 MHz) δ 1.35 (t, J=7.0, 6H), 1.92 (m, 1H), 2.20 (m, 1H), 2.78-2.99 (m, 3H), 3.06 (dd, J=12.7, 3.7, 1H), 3.13 (dd, J=12.7, 6.2, 1H), 3.20 (m, 1H), 4.16-4.23 (m, 4H).

Step E: (R/S)-1-(4-(Nonylphenyl)methyl-3-hydroxy-pyrrolidin-3-yl phosphonic acid, diethyl ester A solution of 60 mg (0.23 mmol) of (R/S)-3-hydroxy-pyrrolidin-3-ylphosphonic acid, diethyl ester (from Step D) and 54 mg (0.23 mmol) of Aldehyde 1 in 1.5 mL of $CH_2Cl_2$ was treated with 73 mg (0.34 mmol) of sodium triacetoxyborohydride. After 3 h at rt, the reaction was diluted with 25 mL of $CH_2Cl_2$ and washed with 25 mL of 1N $NaHCO_3$. After separating phases, the aqueous layer was extracted with 25 mL of $CH_2Cl_2$. The combined organic layers were washed with 50 mL of sat'd NaCl, dried over $Na_2SO_4$ and concentrated. The residue was purified by flash chromatography using 3:1 v/v hexane/acetone as the eluant to afford 33 mg (32%) of the title compound: $R_F$: 0.31 (7:3 v/v hexane/acetone); $^1$H-NMR (500 MHz) δ 0.89 (t, J=7.0, 3H), 1.27-1.36 (m, 18H), 1.57-1.63 (m, 2H), 1.97 (m, 1H), 2.41-2.54 (m, 2H), 2.59 (t, J=7.7, 2H), 2.85-2.92 (m, 2H), 3.01 (m, 1H), 3.67 (ABq, J=13.1, 2H), 4.16-4.23 (m, 4H), 7.12 (d, J=7.8, 2H), 7.24 (d, J=7.8, 2H).

Step F: (R/S)-1-(4-Nonylbenzyl)-3-hydroxypyrrolidin-3-ylphosphonic acid

A solution of 33 mg (0.075 mmol) of (R/S)-1-(4-nonylbenzyl)-3-hydroxypyrrolidin-3-ylphosphonic acid, diethyl ester (from Step E) in 1 mL of chloroform was treated with 0.053 mL (0.37 mmol) of iodotrimethylsilane. The reaction was allowed to stir at rt for 1 h. The reaction was quenched with MeOH and concentrated several times from MeOH. The residue was purified using LC-2 to afford 4.6 mg (16%) of the title compound: ESI-MS 385 (M+H); LC-1: 3.01 min.

Examples 2-10

EXAMPLES 2-10 were prepared using procedures analogous to those described in EXAMPLE 1 substituting the appropriate Aldehyde in Step E. TMS-Br was substituted in Step F with substrates containing TMS-I sensitive functionality (See EXAMPLE 11, Step D). In EXAMPLES 5 and 6 enantiomers were resolved after Step E by preparative chiral HPLC (Chiralpak AD 2×25 cm HPLC column, 9:1 v/v hexane/EtOH, flow rate=9.0 mL/min, λ=210 nM).

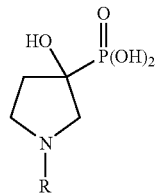

| EXAMPLE # | R | HPLC Method | HPLC RT (min) | ESI-MS (M + H) |
|---|---|---|---|---|
| 2 | ![benzyl-OC8H17 para] | LC-1 | 2.7 | 386 |
| 3 | ![benzyl-OC8H17 meta] | LC-1 | 2.7 | 386 |

-continued
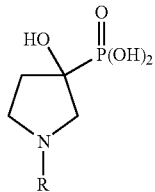
| EXAMPLE # | R | HPLC Method | HPLC RT (min) | ESI-MS (M + H) |
|---|---|---|---|---|
| 4 | 3-OCH₃, 4-OC₈H₁₇, 5-Br benzyl | LC-1 | 3.0 | 496 |
| 5 Enantiomer 1 | 3-OC₂H₅, 4-OC₈H₁₇ benzyl | LC-1 | 2.8 | 430 |
¹H-NMR (500 MHz, CD₃OD) δ 0.92(t, J=7.0, 3H), 1.20-1.54(m, 9H), 1.79-1.84 (m, 2H), 2.23(m, 1H), 2.35(m, 1H), 2.43(m, 1H), 2.68(m, 1H), 3.41-3.50(m, 2H), 3.58(m, 1H), 3.68(m, 1H), 3.75-3.79(m, 2H), 4.04(t, J=6.4, 2H), 4.11-4.15(m, 2H), 4.38(ABq, J=12.9, 2H), 7.02-7.09(m, 2H), 7.17(s, 1H)
| 6 Enantiomer 2 | 3-OC₂H₅, 4-OC₈H₁₇ benzyl | LC-1 | 2.8 | 430 |
|---|---|---|---|---|
| 7 | 3,5-diBr, 4-OC₈H₁₇ benzyl | LC-1 | 3.1 | 544 |
¹H-NMR (500 MHz, CD₃OD) δ 0.93(t, J=6.8, 3H), 1.20-1.46(m, 9H), 1.55-1.61 (m, 2H), 1.86-1.92(m, 2H), 2.23-2.35(m, 2H), 2.72(m, 1H), 3.47-3.79(br m, 3H), 4.06(t, J=6.4, 2H), 4.44-4.50(m, 2H), 7.86(s, 2H)
| 8 | 4-(C(O)C₈H₁₇)benzyl | LC-1 | 2.6 | 398 |
|---|---|---|---|---|
| 9 | 4-(C(O)OC₇H₁₅)benzyl | LC-1 | 2.5 | 400 |
| 10 | 4-(O(CH₂)₄Ph)benzyl | LC-1 | 2.4 | 406 |

Example 11

(R/S)-1-(4-Nonylphenyl)methyl-pyrrolidin-3-yl phosphonic acid

Step A: (R/S)-1-Benzyl-pyrrolidin-3-yl phosphonic acid, diethyl ester

A solution of 6.0 g (36.6 mmol) of diethyl vinylphosphonate and 11 mL (44 mmol) of N-(methoxymethyl)-N-(trimethylsilylmethyl)benzylamine in 150 mL of $CH_2Cl_2$ at 0° C. was stirred for 30 min. The reaction mixture was washed with 150 mL of 1N $NaHCO_3$ and 150 mL of sat'd NaCl. The organic layer was dried over $Na_2SO_4$ and concentrated. The residue was purified on a 40L Biotage column using 3:2 and 1:1 v/v hexane/acetone as the gradient to afford 9.44 g (87%) of the title compound as a pale yellow oil: $R_F$: 0.24 (3:2 v/v hexane/acetone); $^1$H-NMR (500 MHz) δ 1.32 (t, J=7.0, 6H), 2.04-2.12 (m, 2H), 2.39-2.58 (m, 3H), 2.83 (m, 1H), 2.97 (m, 1H), 3.64 (s, 2H), 4.06-4.16 (m, 4H), 7.24-7.34 (m, 5H); ESI-MS 298 (M+H); LC-1: 1.2 min.

Step B: (R/S)-Pyrrolidin-3-ylphosphonic acid, diethyl ester

A mixture of 3 g (10 mmol) of (R/S)-1-benzyl-pyrrolidin-3-ylphosphonic acid, diethyl ester (from Step A), 9.5 g (150 mmol) of ammonium formate and 1.0 g of 10% palladium on charcoal in 60 mL of MeOH was warmed to 40° C. for 1.5 h. The reaction was cooled, filtered through a pad of celite and concentrated. The mixture was partitioned between 75 mL of 1N NaOH and 100 mL of $CH_2Cl_2$. After separating layers, the aqueous phase was extracted with 3×100 mL of $CH_2Cl_2$. The combined organic layers were dried over $Na_2SO_4$ and concentrated. The residue was purified on a 40M Biotage column using 90:10:1 v/v/v $CH_2Cl_2$/MeOH/$NH_4OH$ as the eluant to afford the title compound as a pale yellow oil: $R_F$: 0.13 (95:5:0.5 v/v/v $CH_2Cl_2$MeOH/$NH_4OH$); $^1$H-NMR (500 MHz) δ 1.22 (t, J=7.1, 6H), 1.81 (m, 1H), 1.95 (m, 1H), 2.25 (m, 1H), 2.73 (m, 1H), 2.89-2.99 (m, 3H), 4.06-4.16 (m, 4H).

Step C: (R/S)-1-(4-Nonylphenyl)methyl-pyrrolidin-3-ylphosphonic acid, diethyl ester A solution of 41 mg (0.19 mmol) of (R/S)-pyrrolidin-3-yl phosphonic acid, diethyl ester (from Step B) and 43 mg (0.18 mmol) of Aldehyde 1 in 1 mL of $CH_2Cl_2$ was treated with 57 mg (0.27 mmol) of sodium triacetoxyborohydride. After stirring at rt overnight, the reaction was diluted with 25 mL of $CH_2Cl_2$ and washed with 25 mL of 1N $NaHCO_3$. After separating phases, the aqueous layer was extracted with 25 mL of $CH_2Cl_2$. The combined organic layers were washed with 50 mL of sat'd NaCl, dried over $Na_2SO_4$ and concentrated. The residue was purified by flash chromatography using 49:1 v/v $CH_2Cl_2$/MeOH as the eluant to afford 67 mg (99%) of the title compound: $R_F$: 0.39 (19:1 v/v $CH_2Cl_2$/MeOH); $^1$H-NMR (500 MHz) δ 0.90 (t, J=7.0, 3H), 1.20-1.35 (m, 17H), 1.59-1.65 (m, 2H), 2.04-2.13 (m, 3H), 2.41-2.62 (m, 5H), 2.85 (m, 1H), 2.99 (m, 1H), 3.62 (s, 2H), 4.08-4.17 (m, 4H), 7.14 (d, J=8.0, 2H), 7.24 (d, J=8.0, 2H).

Step D: (R/S)-1-(4-Nonylbenzyl)-pyrrolidin-3-ylphosphonic acid

A solution of 67 mg (0.16 mmol) of (R/S)-1-(4-nonylbenzyl)-pyrrolidin-3-ylphosphonic acid, diethyl ester (from Step C) in 1 mL of acetonitrile was treated with 0.094 mL (0.71 mmol) of bromotrimethylsilane. The reaction was allowed to stir at 80° C. for 1 h. The reaction was quenched with MeOH and concentrated several times from MeOH. The residue was purified by LC-2 to afford 27 mg (46%) of the title compound: ESI-MS 368 (M+H); LC-1: 3.1 min.

Examples 12-17

EXAMPLES 12-17 were prepared using procedures analogous to those described in EXAMPLE 11 substituting the appropriate Aldehyde in Step C. In EXAMPLES 15 and 16 enantiomers were were resolved after Step E by preparative chiral HPLC (Chiralcel OD 2×25 cm HPLC column, 19:1 v/v hexane/iPrOH, flow rate=9.0 mL/min, λ=210 nM).

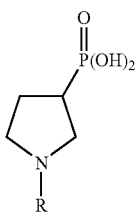

| EXAMPLE # | R | HPLC Method | HPLC RT (min) | ESI-MS (M + H) |
|---|---|---|---|---|
| 12 | ⟨4-OC₈H₁₇-benzyl⟩ | LC-1 | 2.8 | 370 |
| 13 | ⟨3-OC₈H₁₇-benzyl⟩ | LC-1 | 2.7 | 370 |

-continued

[Structure: pyrrolidine with N-R substituent and 3-position P(O)(OH)₂ phosphonic acid group]

| EXAMPLE # | R | HPLC Method | HPLC RT (min) | ESI-MS (M + H) |
|---|---|---|---|---|
| 14 | [benzyl with 3-OC₂H₅ and 4-OC₈H₁₇ substituents] | — | — | — |

¹H-NMR (500 MHz, CD₃OD) δ 0.92(t, J=7.0, 3H), 1.34-1.54(m, 10H), 1.79-1.84 (m, 2H), 2.18(m, 1H), 2.32-2.45(m, 2H), 2.69(m, 1H), 2.88(m, 1H), 3.22-3.37(m, 2H), 3.47-3.62(m, 2H), 3.73(m, 1H), 4.04(t, J=6.4, 2H), 4.13(q, J=7.0, 2H), 4.32-4.37(m, 2H), 7.02-7.08(m, 2H), 7.16(s, 1H)

| 15 Enantiomer 1 | [benzyl with 3,5-diBr and 4-OC₈H₁₇ substituents] | LC-1 | 3.2 | 528 |

¹H-NMR (500 MHz, CD₃OD) δ 0.93(t, J=6.9, 3H), 1.34-1.46(m, 8H), 1.55-1.61 (m, 2H), 1.86-1.95(m, 2H), 2.25-2.47(m, 2H), 2.72(m, 1H), 3.28(m, 1H), 3.63-3.79 (m, 3H), 4.06(t, J=6.4, 2H), 4.44(s, 2H), 7.87(s, 2H)

| 16 Enantiomer 2 | [benzyl with 3,5-diBr and 4-OC₈H₁₇ substituents] | LC-1 | 3.1 | 528 |
| 17 | [benzyl with 4-O(CH₂)₄Ph substituent] | LC-1 | 2.4 | 390 |

Example 18

(R/S)-1-{4-[(4-Phenyl-5-trifluoromethyl-2-thienyl)methoxy]benzyl}-pyrrolidin-3-yl carboxylic acid Step A: (R/S)-1-Benzyl-pyrrolidin-3-yl carboxylic acid, benzyl ester A solution of 10.0 g (61.6 mmol) of benzyl acrylate and 19 mL (74.2 mmol) of N-(methoxymethyl)-N-(trimethylsilylmethyl)benzylamine in 75 mL of CH₂Cl₂ at 0° C. was treated with 0.5 mL (6.5 mmol) of TFA while maintaining the internal temperature at less than 3° C. The reaction was warmed to rt and stirred for 2.5 h. The reaction mixture was washed with 250 mL of 1N NaHCO₃ and 250 mL of sat'd NaCl. The organic layer was dried over Na₂SO₄ and concentrated. The residue was purified on a 40L Biotage column using 19:1 v/v hexane/acetone as the eluant to afford 18 g (99%) of the title compound as a light yellow oil: R$_F$: 0.28 (9:1 v/v hexane/acetone); ¹H-NMR (500 MHz) δ 2.15-2.20 (m, 2H), 2.60 (m, 1H), 2.73-2.77 (m, 2H), 3.02 (m, 1H), 3.13 (m, 1H), 3.66-3.73 (m, 2H), 5.17 (s, 2H), 7.28-7.42 (m, 5H).

Step B: (R/S)-1-Benzyloxycarbonyl-pyrrolidin-3-yl carboxylic acid, benzyl ester

A solution of 18 g (61 mmol) of (R/S)-1-benzyl-pyrrolidin-3-yl carboxylic acid, benzyl ester (from Step A) in 100 mL of CH₂Cl₂ at 0° C. was treated with 21.3 mL (231 mmol) of benzyl chloroformate while maintaining the internal temperature at less than 6° C. The reaction was allowed to warm to rt overnight. After 24 hours at rt, an additional 10 mL (10.8 mmol) of benzyl chloroformate was added. After 24 hours of stirring at rt, the reaction was concentrated. The residue was purified on a 40L Biotage column using 19:1 v/v hexane/acetone as the eluant to afford 8.42 g (39%) of the title compound as a colorless oil: R$_F$: 0.14 (9:1 v/v hexane/acetone); ¹H-NMR (500 MHz) δ 2.19-2.22 (m, 2H), 3.15 (m, 1H), 3.45-3.75 (m, 4H), 5.13-5.20 (m, 4H), 7.33-7.41 (m, 10H).

Step C: (R/S)-Pyrrolidin-3-yl carboxylic acid

A mixture of 8.4 g (24.7 mmol) of (R/S)-1-benzyloxycarbonyl-pyrrolidin-3-yl carboxylic acid, benzyl ester (from Step B) and 2.86 g of 10% palladium on charcoal in 80 mL of MeOH was hydrogenated at atmospheric pressure using a balloon of hydrogen for 6.5 h. The reaction was filtered through a pad of Celite and concentrated to afford 2.72 g (95%) of the title compound as a white solid: $^1$H-NMR (500 MHz, $CD_3OD$) δ 2.17-2.26 (m, 2H), 3.03 (m, 1H), 3.24-3.38 (m, 3H), 3.51 (m, 1H).

Step D: (R/S)-1-{4-[(4-Phenyl-5-trifluoromethyl-2-thienyl)methoxy]benzyl}-pyrrolidin-3-yl carboxylic acid A mixture of 17.5 mg (0.15 mmol) of (R/S)-pyrrolidin-3-yl carboxylic acid (from Step C), 78 mg (0.21 mmol) of Aldehyde 16 and 9 mg (0.14 mmol) of sodium cyanoborohydride in 2 mL of MeOH was stirred at rt overnight. The reaction was concentrated and purified by flash chromatography using 19:1 v/v $CH_2Cl_2$/MeOH, then 85:15:1.5 v/v/v $CH_2Cl_2$/MeOH/$NH_4OH$ as the eluant to afford 42 mg (63%) of the title compound as a white foam: $R_F$: 0.29 (85:15:1.5 v/v/v $CH_2Cl_2$/MeOH/$NH_4OH$); $^1$H-NMR (500 MHz, CD3OD) δ 2.23-2.35 (m, 2H), 3.09 (m, 1H), 3.26-3.41 (m, 3H), 3.53 (m, 1H), 4.30 (ABq, J=13.0, 2H), 5.38 (s, 2H), 7.13 (d, J=8.5, 2H), 7.22 (s, 1H), 7.39-7.45 (m, 5H), 7.48 (d, J=8.5, 2H); ESI-MS 462 (M+H); LC-1: 2.7 min.

Examples 19-33

EXAMPLES 19-33 were prepared using procedures analogous to those described in EXAMPLE 18 substituting the appropriate Aldehyde in Step D.

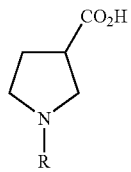

| EXAMPLE # | R | HPLC Method | HPLC RT (min) | ESI-MS (M + H) |
|---|---|---|---|---|
| 19 | ![4-C9H19-benzyl] | LC-1 | 2.8 | 332 |

$^1$H-NMR (500 MHz) δ 0.91(t, J=6.9, 3H), 1.30-1.34(m, 12H), 1.60-1.63(m, 2H), 2.33-2.41(m, 2H), 2.60-2.63(m, 2H), 3.09-3.29(m, 4H), 3.73(m, 1H), 4.20(ABq, J=12.5, 2H), 7.21(d, J=7.7, 2H), 7.44(d, J=7.7, 2H)

| | | | | |
|---|---|---|---|---|
| 20 | ![4-C10H21-benzyl] | LC-1 | 3.0 | 346 |
| 21 | ![4-OC8H17-benzyl] | LC-1 | 3.0 | 334 |

$^1$H-NMR (500 MHz, $CD_3OD$) δ 0.91(t, J=7.0, 3H), 1.31-1.50(m, 10H), 1.75-1.80 (m, 2H), 2.22-2.33(m, 2H), 3.08(m, 1H), 3.25-3.40(m, 3H), 3.52(m, 1H), 3.99(t, J=6.4, 2H), 4.28(ABq, J=13.0, 2H), 6.97(d, J=8.6, 2H), 7.41(d, J=8.6, 2H)

| | | | | |
|---|---|---|---|---|
| 22 | ![3-OCH3,4-OC8H17-benzyl] | LC-1 | 2.9 | 364 |

$^1$H-NMR (500 MHz, $CD_3OD$) δ 0.91(t, J=6.9, 3H), 1.31-1.51(m, 10H), 1.76-1.82 (m, 2H), 2.24-2.37(m, 2H), 3.17(m, 1H), 3.29-3.43(m, 3H), 3.56(m, 1H), 3.87(s, 3H), 4.01(t, J=6.5, 2H), 4.29(ABq, J=12.8, 2H), 6.98(d, J=8.2, 1H), 7.03(dd, J=8.2, 1.7, 1H), 7.12(d, J=1.7, 1H)

| | | | | |
|---|---|---|---|---|
| 23 | ![3-CH3,4-OC8H17-benzyl] | LC-1 | 3.3 | 348 |

-continued

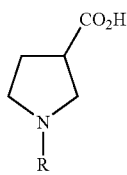

| EXAMPLE # | R | HPLC Method | HPLC RT (min) | ESI-MS (M + H) |
|---|---|---|---|---|
| 24 | 4-(octyloxy)naphthalen-1-ylmethyl | LC-1 | 3.5 | 384 |
| 25 | 2-chloro-4-(octyloxy)benzyl | LC-1 | 3.2 | 368 |
| 26 | 3-chloro-4-(octyloxy)benzyl | LC-1 | 3.2 | 368 |
| 27 | 4-((geranyl)oxy)benzyl | LC-1 | 2.9 | 358 |
| 28 | 4-(5-(4-phenyl-5-(trifluoromethyl)thiophen-2-yl)-1,2,4-oxadiazol-3-yl)benzyl | LC-1 | 3.2 | 500 |

$^1$H-NMR (500 MHz, CD$_3$OD) δ 2.26-2.37(m, 2H), 3.13(m, 1H), 3.25-3.43(m, 3H), 3.52(m, 1H), 4.37(ABq, J=12.9, 2H), 7.49-7.50(m, 5H), 7.69(d, J=8.1, 2H), 8.00 (s, 1H), 8.16(d, J=8.1, 2H)

| 29 | 4-((3,7-dimethyloctyl)oxy)benzyl | LC-1 | 3.0 | 362 |

EXAMPLE 29 was prepared by catalytic hydrogenation of EXAMPLE 27 using a procedure analogous to that described in EXAMPLE 18, Step C.

| 30 | 4-((3,5-bis(trifluoromethyl)benzyl)oxy)benzyl | LC-1 | 2.9 | 448 |

-continued

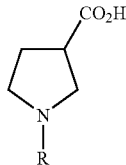

| EXAMPLE # | R | HPLC Method | HPLC RT (min) | ESI-MS (M + H) |
|---|---|---|---|---|
| | $^1$H-NMR (500 MHz, CD$_3$OD) δ 2.23-2.34(m, 2H), 3.09(m, 1H), 3.25-3.40(m, 3H), 3.53(m, 1H), 4.30(ABq, J=13.0, 2H), 5.31(s, 2H), 7.14(d, J=8.6, 2H), 7.48(d, J= 8.6, 2H), 7.94(s, 1H), 8.07(s, 2H) | | | |
| 31 | (4-benzyloxymethyl-benzothiophene structure) | — | — | 368 |
| 32 | (4-benzyloxymethyl-benzofuran structure) | — | — | 352 |
| 33 | (4-benzyloxymethyl-1,5-diphenylpyrazole structure) | — | — | 454 |

Example 35

(R/S)-1-(4-Nonylphenyl)methyl-3-fluoro-pyrrolidin-3-yl carboxylic acid

Step A: (R/S)-1-Benzyl-pyrrolidin-3yl carboxylic acid, methyl ester

The title compound was prepared using a procedure analogous to that described in EXAMPLE 18, Step A substituting methyl acrylate for benzyl acrylate: $R_F$: 0.29 (9:1 v/v hexane/acetone); $^1$H-NMR (500 MHz) δ 2.10-2.14 (m, 2H), 2.55 (m, 1H), 2.66 (m, 1H), 2.75 (m, 1H), 2.94 (m, 1H), 3.06 (m, 1H), 3.65 (s, 2H), 3.69 (s, 3H), 7.25-7.35 (m, 5H).

Step B: (R/S)-Pyrrolidin-3-yl carboxylic acid, methyl ester hydrochloride salt

A solution of 0.52 g (2.3 mmol) of (R/S)-1-benzyl-pyrrolidin-3-yl carboxylic acid, methyl ester (from Step A) in 5 mL of 1,2-dichloroethane was treated with 0.3 mL (2.7 mmol) of 1-chloroethyl chloroformate (ACE-Cl). The resulting mixture was stirred at rt for 3 h, then at reflux for 30 min. The reaction was cooled and concentrated. The residue was warmed to reflux in 5 mL of MeOH for 1 h. The reaction was cooled and concentrated. The crude product was used in Step C without further purification.

Step C: (R/S)-1-(4-Nonylphenyl)methyl-pyrrolidin-3-yl carboxylic acid, methyl ester The title compound was prepared using an analogous procedure described in EXAMPLE 1, Step E substituting (R/S)-pyrrolidin-3-yl carboxylic acid, methyl ester hydrochloride salt (from Step B) for (R/S)-3-hydroxypyrrolidin-3-ylphosphonic acid, diethyl ester and using DIEA to neutralize the hydrochloride salt: $R_F$: 0.44 (4:1 v/v hexane/acetone); $^1$H-NMR (500 MHz) δ 0.91 (t, J=6.9, 3H), 1.30-1.35 (m, 12H), 1.60-1.66 (m, 2H), 2.13-2.17 (m, 2H), 2.54-2.69 (m, 4H), 2.80 (m, 1H), 2.99 (m, 1H), 3.09 (m, 1H), 3.66 (s, 2H), 3.72 (s, 3H), 7.16 (d, J=8.0, 2H), 7.27 (d, J=8.0, 2H).

Step D: (R/S)-1-(4-Nonylphenyl)methyl-3-fluoropyrrolidin-3-yl carboxylic acid, methyl ester To a solution of 1 mL (0.32 mmol) of 0.32M lithium diisopropylamide in THF at −78° C. was added 90 mg (0.26 mmol) of (R/S)-1-1-(4-nonylphenyl) methylbenzyl)-pyrrolidin-3-yl carboxylic acid, methyl ester (from Step C) in 1.5 mL of THF while maintaining the internal temperature at less −70° C. After 15 min, 111 mg (0.35 mmol) of fluorobenzenesulfonimide in 0.5 mL THF was added while maintaining the internal temperature at less −68° C. After stirring for 15 min, the reaction was warmed to 0° C. and quenched with 0.1N HCl. The reaction mixture was poured into 50 mL of Et$_2$O and washed with 50 mL of 1N NaHCO$_3$ and 50 mL of sat'd NaCl. The organic phase was dried over MgSO$_4$ and concentrated. The residue was purified by flash chromatography using 19:1 v/v hexane/acetone as the eluant to afford 47 mg (50%) of the title compound as a colorless film: R$_F$: 0.36 (9:1 v/v hexane/acetone); $^1$H-NMR (500 MHz) δ 0.91 (t, J=6.8, 3H), 1.30-1.35 (m, 12H), 1.60-1.66 (m, 2H), 2.28 (m, 1H), 2.49 (m, 1H), 2.62 (t, J=7.8, 2H), 2.69 (m, 1H), 2.95-3.10 (m, 3H), 3.69 (ABq, J=12.8, 2H), 3.83 (s, 3H), 7.16 (d, J=7.8, 2H), 7.27 (d, J=7.8, 2H).

Step E: (R/S)-1-(4-Nonylphenyl)methyl-3-fluoropyrrolidin-3-yl carboxylic acid

A solution of 46 mg (0.12 mmol) of (R/S)-1-(4-nonylphenyl)methyl-3-fluoropyrrolidin-3-yl carboxylic acid, methyl ester (from Step D) in 3 mL of EtOH was treated with 0.16 mL (0.16 mmol) of 1N NaOH and stirred overnight at rt. The reaction was neutralized with 2 mL of pH 7 buffer and concentrated. Toluene was added and the resulting mixture was concentrated. The residue was purified by flash chromatography using 19:1 v/v CH$_2$Cl$_2$/MeOH, then 90:10:1 v/v/v CH$_2$Cl$_2$/MeOH/NH$_4$OH as the eluant to afford 38 mg (86%) of the title compound as a white, waxy solid: R$_F$: 0.21 (85:15:1.5 v/v/v CH$_2$Cl$_2$/MeOH/NH$_4$OH); $^1$H-NMR (500 MHz) δ 0.79 (t, J=6.8, 3H), 1.18-1.23 (m, 12H), 1.48-1.52 (m, 2H), 2.30 (m, 1H), 2.47-2.59 (m, 3H), 3.29-3.44 (m, 3H), 3.73 (m, 1H), 3.87 (br m, 1H), 4.17 (ABq, J=12.9, 2H), 7.12 (d, J=7.9, 2H), 7.28 (d, J=7.9, 2H); ESI-MS 350 (M+H); LC-1: 3.3 min.

Example 36

(R/S)-1-(4-Nonylphenyl)methyl-3-hydroxypyrrolidin-3-yl carboxylic acid

Step A: (R/S) 1-(4-Nonylphenyl)methyl-3-hydroxypyrrolidin-3-yl carboxylic acid methyl ester To a solution of 0.52 mL (0.52 mmol) of 1.0M sodium hexamethylsilazide in THF at −78° C. was added 153 mg (0.44 mmol) of (R/S)-1-(4-nonylphenyl)methyl-pyrrolidin-3-yl carboxylic acid, methyl ester (from EXAMPLE 34, Step C) in 1 mL of THF while maintaining the internal temperature at less −72° C. After 20 min, 172 mg (0.65 mmol) of 2-(phenylsulfonyl)-3-phenyloxaziridine (Davis Reagent) in 1 mL of THF was added while maintaining the internal temperature at less −69° C. After stirring for 1.25 h at −78° C., the reaction was quenched with 1N NaHCO$_3$ and warmed to rt. After removing volatiles under reduced pressure, the reaction mixture was diluted with 50 mL of 1N NaHCO$_3$ and 50 mL of sat'd NaCl. The aqueous phase was extracted with 3×50 mL of CH$_2$Cl$_2$. The combined organic layers were dried over Na$_2$SO$_4$ and concentrated. The residue was purified by flash chromatography using 4:1 v/v hexane/EtOAc and 4:1 v/v hexane/acetone as the gradient to afford 11 mg (7%) of the title compound as a colorless film: R$_F$: 0.39 (4:1 v/v hexane/acetone); $^1$H-NMR (500 MHz) δ 0.90 (t, J=6.8, 3H), 1.28-1.33 (m, 12H), 1.59-1.64 (m, 2H), 2.02 (m, 1H), 2.42 (m, 1H), 2.60 (t, J=7.8, 2H), 2.67 (m, 1H), 2.86 (ABq, J=10.1, 2H), 2.97 (m, 1H), 3.69 (s, 2H), 3.82 (s, 3H), 7.14 (d, J=7.9, 2H), 7.26 (d, J=7.9, 2H).

Step B: (R/S)-1-(4-Nonylphenyl)methyl-3-hydroxypyrrolidin-3-yl carboxylic acid

The title compound was prepared using an analogous procedure described in EXAMPLE 34, Step E substituting (R/S)-1-(4-nonylphenyl)methyl-3-hydroxypyrrolidin-3-yl carboxylic acid, methyl ester (from Step A) for (R/S)-1-(4-nonylphenyl)methyl-3-fluoropyrrolidin-3-yl carboxylic acid, methyl ester: R$_F$: 0.15 (90:10:1 v/v/v CH$_2$Cl$_2$/MeOH/NH$_4$OH); $^1$H-NMR (500 MHz, CD$_3$OD) δ 0.89 (t, J=6.9, 3H), 1.28-1.33 (m, 12H), 1.60-1.63 (m, 2H), 2.10 (m, 1H), 2.49 (m, 1H), 2.64 (t, J=7.7, 2H), 3.25 (m, 1H), 3.49-3.62 (m, 3H), 4.38 (ABq, J=13.0, 2H), 7.28 (d, J=7.8, 2H), 7.42 (d, J=7.8, 2H); ESI-MS 348 (M+H); LC-1: 3.0 min.

Example 37

(R/S)-1-(4-Nonylphenyl)methyl-pyrrolidin-3-yl acetic acid

Step A: (R/S)-1-(4-Nonylphenyl)methyl-pyrrolidin-3-ylacetic acid, tert-butyl ester The title compound was prepared using an analogous procedure described in EXAMPLE 1, Step E substituting (R/S)-pyrrolidin-3-yl acetic acid, tert-butyl ester hydrochloride salt for (R/S)-3-hydroxypyrrolidin-3-ylphosphonic acid, diethyl ester and using DIEA to neutralize the hydrochloride salt: R$_F$: 0.53 (4:1 v/v hexane/acetone); $^1$H-NMR (500 MHz) δ 0.90 (t, J=6.8, 3H), 1.28-1.64 (m, 25H), 2.09 (m, 1H), 2.26-2.37 (m, 3H), 2.58-2.69 (m, 4H), 2.89 (m, 1H), 3.61-3.64 (m, 2H), 7.14 (d, J=7.4, 2H), 7.26 (d, J=7.4, 2H).

Step B: (R/S)-1-(4-Nonylphenyl)methyl-pyrrolidin-3-yl acetic acid

A solution of 50.5 mg (0.12 mmol) of (R/S)-1-(4-nonylphenyl)methyl-pyrrolidin-3-yl acetic acid, tert-butyl ester (from Step A) in formic acid at 55° C. was stirred for 2.25 h. Volatiles were removed under reduced pressure. The residue was purified by flash chromatography using 19:1 v/v CH$_2$Cl$_2$/MeOH, then 85:15:1.5 v/v/v CH$_2$Cl$_2$/MeOH/NH$_4$OH as the eluant to afford 41 mg (94%) of the title compound as a sticky, waxy film: R$_F$: 0.31 (85:15:1.5 v/v/v CH$_2$Cl$_2$/MeOH/NH$_4$OH); $^1$H-NMR (500 MHz, CD$_3$OD) δ 0.90 (t, J=6.9, 3H), 1.29-1.33 (m, 12H), 1.61-1.64 (m, 2H), 1.77 (m, 1H), 2.26-2.45 (m, 3H), 2.64 (t, J=7.7, 2H), 2.71 (m, 1H), 3.08 (m, 1H), 3.23 (m, 1H), 3.38-3.44 (m, 2H), 4.28 (s, 2H), 7.28 (d, J=8.1, 2H), 7.39 (d, J=8.1, 2H); ESI-MS 346 (M+H); LC-1: 3.3 min.

Example 38

(R/S)-1-{4-[(4-Phenyl-5-trifluoromethyl-2-thienyl)methoxy]benzyl}-pyrrolidin-3-ylacetic acid The title compound was prepared using procedures analogous to those described in EXAMPLE 36 substituting Aldehyde 16 for Aldehyde 1 in Step A: R$_F$: 0.29 (85:15:1.5 v/v/v CH$_2$Cl$_2$/MeOH/NH$_4$OH); $^1$H-NMR (500 MHz, CD$_3$OD) δ 1.77 (m, 1H), 2.26-2.46 (m, 3H), 2.71 (m, 1H), 3.07 (m, 1H), 3.23 (m, 1H), 3.37-3.34 (m, 2H), 4.28 (s, 2H), 5.38 (s, 2H), 7.13 (d, J=8.7, 2H), 7.23 (s, 1H), 7.40-7.47 (m, 7H); ESI-MS 476 (M+H); LC-1: 3.0 min.

Example 39

(R/S)-5-[1-(4-Nonylphenyl)methylpyrrolidin-3-yl]-1H-tetrazole

Step A: (R/S)-1-Benzyloxycarbonyl-3-cyano pyrrolidine

The title compound was prepared using analogous procedures described in EXAMPLE 18 (Steps A and B) substituting acrylonitrile for benzyl acrylate in Step A: $R_F$: 0.19 (4:1 v/v hexane/acetone); $^1$H-NMR (500 MHz) δ 2.18-2.28 (m, 2H), 3.12 (m, 1H), 3.53 (m, 1H), 3.61-3.78 (m, 3H), 5.16 (d, J=3.0, 2H), 7.32-7.42 (m, 5H).

Step B: (R/S)-5-[1-Benzyloxycarbonyl-pyrrolidin-3-yl]-1H-tetrazole

A mixture of 1.8 g (7.8 mmol) of (R/S)-1-benzyloxycarbonyl-3-cyano pyrrolidine (from Step A), 1.5 g (23 mmol) of sodium azide and 1.25 g (23 mmol) of ammonium chloride in 70 mL of DMF was stirred at 105° C. overnight. After cooling to rt, the reaction was poured into 150 mL of $CH_2Cl_2$ and washed with 150 mL of 1N HCl and 2×150 mL of $H_2O$. The organic phase was dried over $MgSO_4$ and concentrated. The residue was purified on a 40M Biotage column using 80:20:1 v/v/v $CH_2Cl_2$/EtOAc/HOAc as the eluant to afford 670 mg (31%) of the title compound: $R_F$: 0.23 (80:20:1 v/v/v $CH_2Cl_2$/EtOAc/HOAc); $^1$H-NMR (500 MHz) δ 2.29, 2.48 (2m, 2H), 3.54-4.03 (m, 5H), 5.14-5.24 (m, 2H), 7.30-7.37 (m, 5H), 10.43 (br, 1H).

Step C: (R/S)-5-(Pyrrolidin-3-yl)-1H-tetrazole

A mixture of 662 mg (2.4 mmol) of (R/S)-5-[1-benzyloxycarbonyl-pyrrolidin-3-yl]-1H-tetrazole (from Step B) and 220 mg of 10% palladium on charcoal in 5 mL of MeOH was hydrogenated at atmospheric pressure using a balloon of hydrogen for 3 h. The reaction was filtered through a pad of Celite and concentrated to afford the title compound as a white solid: $^1$H-NMR (500 MHz, $CD_3OD$) δ 2.27 (m, 1H), 2.49 (m, 1H), 3.39-3.51 (m, 3H), 3.70 (m, 1H), 3.85 (m, 1H).

Step D: (R/S)-5-[1-(4-Nonylbenzyl)methyl-pyrrolidin-3-yl]-1H-tetrazole

The title compound was prepared using an analogous procedure described in EXAMPLE 18, Step D substituting (R/S)-5-(pyrrolidin-3-yl)-1H-tetrazole (from Step C) for (R/S)-pyrrolidin-3-yl carboxylic acid: 1H-NMR (500 MHz, $CD_3OD$) δ 0.89 (t, J=7.0, 3H), 1.28-1.33 (m, 12H), 1.60-1.63 (m, 2H), 2.33 (m, 1H), 2.55 (m, 1H), 2.64 (t, J=7.6, 2H), 3.47-3.55 (m, 3H), 3.76 (m, 1H), 3.92 (m, 1H), 4.40 (s, 2H), 7.29 (d, J=8.0, 2H), 7.42 (d, J=8.0, 2H); ESI-MS 356 (M+H); LC-1: 3.3 min.

Example 40

1-{4-[(4-Phenyl-5-trifluoromethyl-2-thienyl)methoxy]benzyl}-3-azetidinecarboxylic acid The title compound was prepared by treating a mixture of 0.12 mmol of 3-azetidinecarboxylic acid, 0.1 mmol of Aldehyde 16, 0.007 mL (0.12 mmol) of acetic acid in 2 mL of MeOH with 10 mg (0.16 mmol) of sodium cyanoborohydride and stirring the resulting mixture at rt for 3 h. The product was purified using LC-2: $^1$H NMR (500 MHz, $CD_3OD$) δ 3.34-3.37 (m, 1H), 4.08 (app s, 2H), 4.10 (app s, 2H), 4.22 (s, 2H), 4.86 (s, 2H), 5.35 (s, 2H), 7.10 (app d, J=8.0, 2H), 7.20 (s, 1H), 7.39-7.43 (5H).

Examples 41-45

EXAMPLES 41-45 were prepared using procedures analogous to that described in EXAMPLE 41 substituting the appropriate Aldehyde for Aldehyde 16.

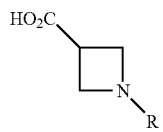

| EXAMPLE # | R | HPLC Method | HPLC RT (min) | ESI-MS (M + H) |
|---|---|---|---|---|
| 41 | ![benzyl-C9H19] -CH2-C6H4-C9H19 | LC-1 | 3.3 | 318 |

$^1$H-NMR (500 MHz, $CD_3OD$) δ 0.89(t, J=6.8, 3H), 1.28-1.32(m, 12H), 1.60-1.62 (m, 2H), 2.63(t, J=7.7, 2H), 3.37(m, 1H), 4.12(s, 2H), 4.13(s, 2H), 4.27(s, 2H), 7.27(d, J=8.0, 2H), 7.35(d, J=8.0, 2H)

| 42 | ![3,5-bis(trifluoromethyl)benzyloxy-benzyl] | LC-1 | 2.9 | 434 |

-continued

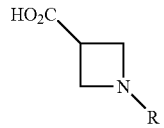

| EXAMPLE # | R | HPLC Method | HPLC RT (min) | ESI-MS (M + H) |
|---|---|---|---|---|

¹H-NMR (500 MHz, CD₃OD) δ 3.35(m, 1H), 4.14(s, 2H), 4.16(s, 2H), 4.28(s, 2H), 5.31(s, 2H), 7.14(d, J=8.6, 2H), 7.42(d, J=8.6, 2H), 7.94(s, 1H), 8.07(s, 2H)

| 43 | 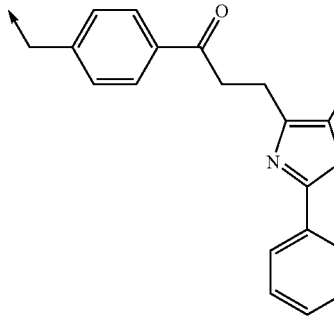 | LC-1 | 2.4 | 405 |
| 44 | 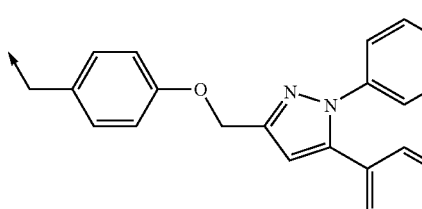 | — | — | 440 |
| 45 | 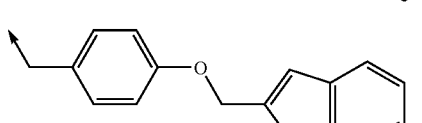 | — | — | 338 |

Examples 46-53

The following compounds were prepared by treating a mixture of 0.12 mmol of either azetidine-3-carboxylic acid or (±)-pyrroldine-3-carboxylic acid, 0.1 mmol of Aldehyde, 7 μL (0.12 mmol) of acetic acid in 2 mL of MeOH with 10 mg (0.16 mmol) of sodium cyanoborohydride and stirring the resulting mixture at rt for 1-3 h. The reaction mixtures were purified using LC-2.

| EXAMPLE | Amino acid | Aldehyde # | LC-1 | MS |
|---|---|---|---|---|
| 46 |  | 19 | 2.9 min | 496 (M + H) |
| 47 |  | 19 | 2.9 min | 482 (M + H) |
| 48 | 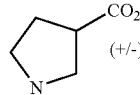 | 18 | 3.1 min | 496 (M + H) |
| 49 | 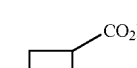 | 18 | 3.1 min | 482 (M + H) |
| 50 | 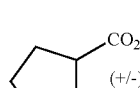 | 21 | 2.9 min | 492 (M + H) |
| 51 | 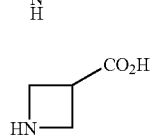 | 21 | 2.9 min | 478 (M + H) |

-continued

| EXAMPLE | Amino acid | Aldehyde # | LC-1 | MS |
|---------|-----------|------------|------|-----|
| 52 | [pyrrolidine-3-carboxylic acid (+/-)] | 20 | 3.1 min | 476 (M + H) |
| 53 | [azetidine-3-carboxylic acid] | 20 | 3.1 min | 462 (M + H) |
| 54 | [azetidine-3-carboxylic acid] | 15 | 3.2 min | 485 (M + H) |

Example 55

(3S,4R or 3R,4S)-1-(4-Nonylbenzyl)4-trifluoromethylpyrrolidin-3-yl carboxylic acid Step A: 4-(Nonyl)benzylamine 4-Nonylbenzoyl chloride (6 g, 20 mmol) and $NH_4OAc$ (6 g,) were suspended in acetone (100 mL) and stirred for 1 h at rt. Water (50 mL) was added and the mixture filtered. The residue was washed with water and dried. The resulting crude amide (2.47 g,~10 mmol) was dissolved in THF (5 mL) and borane dimethylsulfide complex (10 mL of 2M solution, 20 mmol) was added dropwise, while warming to reflux. The mixture was heated for 1 h. then cooled in an ice bath. Methanol (2.5 mL) was added dropwise, followed by 1N HCl in ether (11 mL). The white precipitate of the HCl salt of the benzyl amine was filtered off and washed with ether. The HCl salt was taken up in 2.5N NaOH and ether and the organic layer was separated and dried over $Na_2SO_4$. Evaporation afforded 1.3 g of the title compound.

Step B: N-(Methoxymethyl)-N-(trimethylsilylmethyl)-(4-nonyl)benzylamine

A solution of 1.3 g (6 mmol) of 4-(nonyl)benzylamine (from Step A) and 700 mg (6 mmol) of chloromethyltrimethylsilane in 5 mL of DMSO was stirred at 90° C. for 3 h, then at rt for 16 h. The mixture was partitioned between MTBE and 1N NaOH. The organic layer was separated, washed with sat'd NaCl, dried and concentrated. Flash chromatography using 9:1 v/v hexane/EtOAc as the eluant afforded 700 mg of N-(trimethylsilylmethyl)-4-(nonyl)benzylamine.

A mixture of the crude N-(trimethylsilylmethyl)-4-(nonyl) benzylamine, 140 mg of paraformaldehyde and 15 mg of powdered NaOH in 5 mL of MeOH was stirred at 40° C. for 1 h. The mixture was diluted with ether and aged for 16 h. The mixture was concentrated and dried to afford 700 mg of the title compound: $^1$H NMR (500 MHz, $CD_3OD$) δ: 7.25 (m, 2H); 7.15 (m, 2H); 4.03 (m, 2H); 3.74 (m, 2H); 3.28 (m, 2H); 2.61 (m, 2H); 2.22 (m, 2H); 1.63 (m, 4H); 1.30 (m, 14H); 0.90 (m, 3H); 0.08 (m, 9H).

Step C: 1-(4-(Nonyl)phenyl)methyl-3-(R/S)-carboxy-4-(R/S)-trifluoromethyl pyrrolidine A solution of 50 mg (0.14 mmol) of N-(methoxymethyl)-N-(trimethylsilylmethyl)-(4-nonyl)benzylamine (from Step B) and 20 mg (0.14 mmol) of trans-4,4,4-trifluoro-2-butenoic acid (0.137 mmol) in 1 mL of $CH_2Cl_2$ was treated with 1 drop of TFA and the resulting mixture was heated at 35° C. for 1 h.

The reaction was cooled, concentrated then and then purified using LC-2 to afford the title compound: $^1$H NMR (500 MHz, $CD_3OD$) δ 7.25 (d, J=8, 2H); 7.19 (d, J=8, 2H); 3.87 (m, 2H); 3.54 (m, 1H); 3.27 (m, 4H); 2.93 (m, 1H); 2.61 (m, 2H); 1.62 (m, 2H); 1.30 (m, 14H); 0.90 (t, J=6.7, 3H); ESI-MS 400.3 (M+H).

Examples 56-59

EXAMPLES 56-58 were prepared using procedures analogous to those described in EXAMPLE 55 substituting the appropriate α,β-unsaturated acid in Step C.

| EXAMPLE # | X | Y | ESI-MS (M + H) |
|-----------|---|---|----------------|
| 56 | H | $CF_3$ | 400.3 |
| | $^1$H NMR (500 MHz, $CD_3OD$) δ: 7.43(d, J=8 Hz, 2H); 7.29(d, J=8 Hz 2H); 4.35(s, 2H); 4.04(d, J=12 Hz, 1H); 3.46(m, 1H); 2.65(m, 3H); 2.42(m, 1H); 1.62(m, 2H); 1.30(m, 14H); 0.90(t, J=6.7 3H) | | |
| 57 | $CO_2H$ | H | 375.3 |
| | $^1$H NMR (500 MHz, $CD_3OD$) δ: 7.35(m, 4H); 4.4(m, 1H); 4.12(m, 2H); 3.64(m, 1H); 2.69(m, 5H); 1.64(m, 1H); 1.30(m, 14H); 0.90(m, 3H) | | |
| 58 | H | $CH_2CO_2H$ | 390.3 |
| | $^1$H NMR (500 MHz, $CD_3OD$) δ: 7.36(m, 4H); 4.43(m, 1H); 4.14(m, 3H); 3.79(m, 1H); 3.50(m, 1H); 3.09(m, 2H); 2.70(m, 8H); 3.18(m, 1H); 2.65(m, 2H); 2.3 (m, 2H); 1.61(m, 2H); 1.29(M, 14H); 0.89(m, 3H) | | |

Biological Activity

The $S1P_1$/Edg1, $S1P_3$/Edg3, $S1P_2$/Edg5, $S1P_4$/Edg6 or $S1P_5$/Edg8 activity of the compounds of the present invention can be evaluated using the following assays:

Ligand Binding to Edg/S1P Receptors Assay $^{33}$P-sphingosine-1-phosphate was synthesized enzymatically from $\gamma^{33}$P-ATP and sphingosine using a crude yeast extract with sphingosine kinase activity in a reaction mix containing 50 mM $KH_2PO_4$, 1 mM mercaptoethanol, 1 mM $Na_3VO_4$, 25 mM KF, 2 mM semicarbazide, 1 mM $Na_2EDTA$, 5 mM $MgCl_2$, 50 mM sphingosine, 0.1% TritonX-114, and 1 mCi $\gamma^{33}$P-ATP (NEN; specific activity 3000 Ci/mmol). Reaction products were extracted with butanol and $^{33}$P-sphingosine-1-phosphate was purified by HPLC.

Cells expressing EDG/S1P receptors were harvested with enzyme-free dissociation solution (Specialty Media, Lavallette, N.J.). They were washed once in cold PBS and suspended in binding assay buffer consisting of 50 mM HEPES-Na, pH 7.5, 5 mM $MgCl_2$, 1 mM $CaCl_2$, and 0.5% fatty acid-free BSA. $^{33}$P-sphingosine-1-phosphate was sonicated with 0.1 nM sphingosine-1-phosphate in binding assay buffer; 100 µl of the ligand mixture was added to 100 µl cells ($1\times10^6$ cells/ml) in a 96 well microtiter dish. Binding was performed for 60 min at room temperature with gentle mixing. Cells were then collected onto GF/B filter plates with a Packard Filtermate Universal Harvester. After drying the filter plates for 30 min, 40 μl of Microscint 20 was added to each well and binding was measured on a Wallac Microbeta Scintillation Counter. Non-specific binding was defined as the amount of radioactivity remaining in the presence of 0.5 μM cold sphingosine-1-phosphate.

Alternatively, ligand binding assays were performed on membranes prepared from cells expressing Edg/S1P receptors. Cells were harvested with enzyme-free dissociation solution and washed once in cold PBS. Cells were disrupted by homogenization in ice cold 20 mM HEPES pH 7.4, 10 mM EDTA using a Kinematica polytron (setting 5, for 10 seconds). Homogenates were centrifuged at 48,000×g for 15 min at 4° C. and the pellet was suspended in 20 mM HEPES pH 7.4, 0.1 mM EDTA. Following a second centrifugation, the final pellet was suspended in 20 mM HEPES pH 7.4, 100 mM NaCl, 10 mM $MgCl_2$. Ligand binding assays were performed as described above, using 0.5 to 2 μg of membrane protein.

Agonists and antagonists of Edg/S1P receptors can be identified in the $^{33}$P-sphingosine-1-phosphate binding assay. Compounds diluted in DMSO, methanol, or other solvent, were mixed with probe containing $^{33}$P-sphingosine-1-phosphate and binding assay buffer in microtiter dishes. Membranes prepared from cells expressing Edg/S1P receptors were added, and binding to $^{33}$P-sphingosine-1-phosphate was performed as described. Determination of the amount of binding in the presence of varying concentrations of compound and analysis of the data by non-linear regression software such as MRLCalc (Merck Research Laboratories) or PRISM (GraphPad Software) was used to measure the affinity of compounds for the receptor. Selectivity of compounds for Edg/S1P receptors was determined by measuring the level of $^{33}$P-sphingosine-1-phosphate binding in the presence of the compound using membranes prepared from cells transfected with each respective receptor ($S1P_1$/Edg1, $S1P_3$/Edg3, $S1P_2$/Edg5, $S1P_4$/Edg6, $S1P_5$/Edg8).

$^{35}$S-GTPγS Binding Assay

Functional coupling of S1P/Edg receptors to G proteins was measured in a $^{35}$S-GTPγS binding assay. Membranes prepared as described in the Ligand Binding to Edg/S1P Receptors Assay (1-10 μg of membrane protein) were incubated in a 200 μl volume containing 20 mM HEPES pH 7.4, 100 mM NaCl, 10 mM $MgCl_2$, 5 μM GDP, 0.1% fatty acid-free BSA (Sigma, catalog A8806), various concentrations of sphingosine-1-phosphate, and 125 pM $^{35}$S-GTPγS (NEN; specific activity 1250 Ci/mmol) in 96 well microtiter dishes. Binding was performed for 1 hour at room temperature with gentle mixing, and terminated by harvesting the membranes onto GF/B filter plates with a Packard Filtermate Universal Harvester. After drying the filter plates for 30 min, 40 μl of Microscint 20 was added to each well and binding was measured on a Wallac Microbeta Scintillation Counter.

Agonists and antagonists of S1P/Edg receptors can be discriminated in the $^{35}$S-GTPγS binding assay. Compounds diluted in DMSO, methanol, or other solvent, were added to microtiter dishes to provide final assay concentrations of 0.01 nM to 10 μM. Membranes prepared from cells expressing S1P/Edg receptors were added, and binding to $^{35}$S-GTPγS was performed as described. When assayed in the absence of the natural ligand or other known agonist, compounds that stimulate $^{35}$S-GTPγS binding above the endogenous level were considered agonists, while compounds that inhibit the endogenous level of $^{35}$S-GTPγS binding were considered inverse agonists. Antagonists were detected in a $^{35}$S-GTPγS binding assay in the presence of a sub-maximal level of natural ligand or known S1P/Edg receptor agonist, where the compounds reduced the level of $^{35}$S-GTPγS binding. Determnination of the amount of binding in the presence of varying concentrations of compound was used to measure the potency of compounds as agonists, inverse agonists, or antagonists of S1P/Edg receptors. To evaluate agonists, percent stimulation over basal was calculated as binding in the presence of compound divided by binding in the absence of ligand, multiplied by 100. Dose response curves were plotted using a non-linear regression curve fitting program MRLCalc (Merck Research Laboratories), and $EC_{50}$ values were defined to be the concentration of agonist required to give 50% of its own maximal stimulation. Selectivity of compounds for S1P/Edg receptors was determined by measuring the level of $^{35}$S-GTPγS binding in the presence of compound using membranes prepared from cells transfected with each respective receptor.

Intracellular Calcium Flux Assay

Functional coupling of S1P/Edg receptors to G protein associated intracellular calcium mobilization was measured using FLIPR (Fluorescence Imaging Plate Reader, Molecular Devices). Cells expressing S1P/Edg receptors were harvested and washed once with assay buffer (Hanks Buffered Saline Solution (BRL) containing 20 mM HEPES, 0.1% BSA and 710 μg/ml probenicid (Sigma)). Cells were labeled in the same buffer containing 500 nM of the calcium sensitive dye Fluo-4 (Molecular Probes) for 1 hour at 37° C. and 5% $CO_2$. The cells were washed twice with buffer before plating 1.5× $10^5$ per well (90 μl) in 96 well polylysine coated black microtiter dishes. A 96-well ligand plate was prepared by diluting sphingosine-1-phosphate or other agonists into 200 μl of assay buffer to give a concentration that was 2-fold the final test concentration. The ligand plate and the cell plate were loaded into the FLIPR instrument for analysis. Plates were equilibrated to 37° C. The assay was initiated by transferring an equal volume of ligand to the cell plate and the calcium flux was recorded over a 3 min interval. Cellular response was quantitated as area (sum) or maximal peak height (max). Agonists were evaluated in the absence of natural ligand by dilution of compounds into the appropriate solvent and transfer to the Fluo-4 labeled cells. Antagonists were evaluated by pretreating Fluo-4 labeled cells with varying concentrations of compounds for 15 min prior to the initiation of calcium flux by addition of the natural ligand or other S1P/Edg receptor agonist.

Preparation of Cells Expressing S1P/Edg Receptors

Any of a variety of procedures may be used to clone $S1P_1$/Edg1, $S1P_3$/Edg3, $S1P_2$/Edg5, $S1P_4$/Edg6 or $S1P_5$/Edg8. These methods include, but are not limited to, (1) a RACE PCR cloning technique (Frohman, et al., 1988, *Proc. Natl. Acad. Sci. USA* 85: 8998-9002). 5' and/or 3' RACE may be performed to generate a full-length cDNA sequence; (2) direct functional expression of the Edg/S1P cDNA following the construction of an S1P/Edg-containing cDNA library in an appropriate expression vector system; (3) screening an S1P/Edg-containing cDNA library constructed in a bacteriophage or plasmid shuttle vector with a labeled degenerate oligonucleotide probe designed from the amino acid sequence of the S1P/Edg protein; (4) screening an S1P/Edg-containing cDNA library constructed in a bacteriophage or plasmid shuttle vector with a partial cDNA encoding the S1P/Edg protein. This partial cDNA is obtained by the specific PCR amplification of S1P/Edg DNA fragments through the design of degenerate oligonucleotide primers from the amino acid sequence known for other proteins which are related to the S1P/Edg protein; (5) screening an S1P/Edg-containing cDNA library constructed in a bacteriophage or plasmid shuttle vector with a partial cDNA or oligonucleotide with homology to a mammalian S1P/Edg protein. This strategy may also involve using gene-specific oligonucleotide primers for PCR amplification of S1P/Edg cDNA; or (6) designing 5' and 3' gene specific oligonucleotides using the S1P/Edg nucleotide sequence as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding S1P/Edg.

It is readily apparent to those skilled in the art that other types of libraries, as well as libraries constructed from other cell types-or species types, may be useful for isolating an S1P/Edg-encoding DNA or an S1P/Edg homologue. Other types of libraries include, but are not limited to, cDNA libraries derived from other cells.

It is readily apparent to those skilled in the art that suitable cDNA libraries may be prepared from cells or cell lines which have S1P/Edg activity. The selection of cells or cell lines for use in preparing a cDNA library to isolate a cDNA encoding S1P/Edg may be done by first measuring cell-associated S1P/Edg activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

An expression vector containing DNA encoding an S1P/Edg-like protein may be used for expression of S1P/Edg in a recombinant host cell. Such recombinant host cells can be cultured under suitable conditions to produce S1P/Edg or a biologically equivalent form. Expression vectors may include, but are not limited to, cloning vectors, modified cloning vectors, specifically designed plasmids or viruses. Commercially available mammalian expression vectors may be suitable for recombinant S1P/Edg expression.

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines.

The nucleotide sequences for the various S1P/Edg receptors are known in the art. See, for example, the following:

$S1P_1$/Edg1 Human

Hla, T. and T. Maciag 1990 An abundant transcript induced in differentiating human endothelial cells encodes a polypeptide with structural similarities to G-protein coupled receptors. J. Biol Chem. 265:9308-9313, hereby incorporated by reference in its entirety.

WO91/15583, published on Oct. 17, 1991, hereby incorporated by reference in its entirety.

WO99/46277, published on Sep. 16, 1999, hereby incorporated by reference in its entirety.

$S1P_1$/Edg1 Mouse

WO0059529, published Oct. 12, 2000, hereby incorporated by reference in its entirety.

U.S. Pat. No. 6,323,333, granted Nov. 27, 2001, hereby incorporated by reference in its entirety.

$S1P_1$/Edg1 Rat

Lado, D. C., C. S. Browe, A. A. Gaskin, J. M. Borden, and A. J. MacLennan. 1994 Cloning of the rat edg-1 immediate-early gene: expression pattern suggests diverse functions. *Gene* 149: 331-336, hereby incorporated by reference in its entirety.

U.S. Pat. No. 5,585,476, granted Dec. 17, 1996, hereby incorporated by reference in its entirety.

U.S. Pat. No. 5,856,443, granted Jan. 5, 1999, hereby incorporated by reference in its entirety.

$S1P_3$/Edg3 Human

An, S., T. Bleu, W. Huang, O. G. Hallmark, S. R. Coughlin, E. J. Goetzl 1997 Identification of cDNAs encoding two G protein-coupled receptors for lysosphingolipids FEBS Lett. 417:279-282, hereby incorporated by reference in its entirety.

WO 99/60019, published Nov. 25, 1999, hereby incorporated by reference in its entirety.

U.S. Pat. No. 6,130,067, granted Oct. 10, 2000, hereby incorporated by reference in its entirety.

$S1P_3$/Edg3 Mouse

WO 01/11022, published Feb. 15, 2001, hereby incorporated by reference in its entirety.

$S1P_3$/Edg3 Rat

WO 01/27137, published Apr. 19, 2001, hereby incorporated by reference in its entirety.

$S1P_2$/Edg5 Human

An, S., Y. Zheng, T. Bleu 2000 Sphingosine 1-Phosphate-induced cell proliferation, survival, and related signaling events mediated by G Protein-coupled receptors Edg3 and Edg5. J. Biol. Chem 275: 288-296, hereby incorporated by reference in its entirety.

WO 99/35259, published Jul. 15, 1999, hereby incorporated by reference in its entirety.

WO99/54351, published Oct. 28, 1999, hereby incorporated by reference in its entirety.

WO 00/56135, published Sep. 28, 2000, hereby incorporated by reference in its entirety.

$S1P_2$/Edg5 Mouse

WO 00/60056, published Oct. 12, 2000, hereby incorporated by reference in its entirety.

$S1P_2$/Edg5 Rat

Okazaki, H., N. Ishizaka, T. Sakurai, K. Kurokawa, K. Goto, M. Kumada, Y. Takuwa 1993 Molecular cloning of a novel putative G protein-coupled receptor expressed in the cardiovascular system. Biochem. Biophys. Res. Comm. 190: 1104-1109, hereby incorporated by reference in its entirety.

MacLennan, A. J., C. S. Browe, A. A. Gaskin, D. C. Lado, G. Shaw 1994 Cloning and characterization of a putative G-protein coupled receptor potentially involved in development. Mol. Cell. Neurosci. 5: 201-209, hereby incorporated by reference in its entirety.

U.S. Pat. No. 5,585,476, granted Dec. 17, 1996, hereby incorporated by reference in its entirety.

U.S. Pat. No. 5,856,443, granted Jan. 5, 1999, hereby incorporated by reference in its entirety.

$S1P_4$/Edg6 Human

Graler, M. H., G. Bernhardt, M. Lipp 1998 EDG6, a novel G-protein-coupled receptor related to receptors for bioactive lysophospholipids, is specifically expressed in lymphoid tissue. Genomics 53: 164-169, hereby incorporated by reference in its entirety.

WO 98/48016, published Oct. 29, 1998, hereby incorporated by reference in its entirety.

U.S. Pat. No. 5,912,144, granted Jun. 15, 1999, hereby incorporated by reference in its entirety.

WO 98/50549, published Nov. 12, 1998, hereby incorporated by reference in its entirety.

U.S. Pat. No. 6,060,272, granted May 9, 2000, hereby incorporated by reference in its entirety.

WO 99/35106, published Jul. 15, 1999, hereby incorporated by reference in its entirety.

WO 00/15784, published Mar. 23, 2000, hereby incorporated by reference in its entirety.

WO 00/14233, published Mar. 16, 2000, hereby incorporated by reference in its entirety.

S1P$_4$/Edg6 Mouse

WO 00/15784, published Mar. 23, 2000, hereby incorporated by reference in its entirety.

S1P$_5$/Edg8 Human

Im, D.-S., J. Clemens, T. L. Macdonald, K. R. Lynch 2001 Characterization of the human and mouse sphingosine 1-phosphate receptor, S1P$_5$ (Edg-8): Structure-Activity relationship of sphingosine 1-phosphate receptors. Biochemistry 40:14053-14060, hereby incorporated by reference in its entirety.

WO 00/11166, published Mar. 2, 2000, hereby incorporated by reference in its entirety.

WO 00/31258, published Jun. 2, 2000, hereby incorporated by reference in its entirety.

WO 01/04139, published Jan. 18, 2001, hereby incorporated by reference in its entirety.

EP 1 090 925, published Apr. 11, 2001, hereby incorporated by reference in its entirety.

S1P$_5$/Edg8 Rat

Im, D.-S., C. E. Heise, N. Ancellin, B. F. O'Dowd, G.-J. Shei, R. P. Heavens, M. R. Rigby, T. Hla, S. Mandala, G. McAllister, S. R. George, K. R. Lynch 2000 Characterization of a novel sphingosine 1-phosphate receptor, Edg-8. J. Biol. Chem. 275: 14281-14286, hereby incorporated by reference in its entirety.

WO 01/05829, published Jan. 25, 2001, hereby incorporated by reference in its entirety.

Measurement of Cardiovascular Effects

The effects of compounds of the present invention on cardiovascular parameters can be evaluated by the following procedure:

Adult male rats (approx. 350 g body weight) were instrumented with femoral arterial and venous catheters for measurement of arterial pressure and intravenous compound administration, respectively. Animals were anesthetized with Nembutal (55 mg/kg, ip). Blood pressure and heart rate were recorded on the Gould Po-Ne-Mah data acquisition system. Heart rate was derived from the arterial pulse wave. Following an acclimation period, a baseline reading was taken (approximately 20 minutes) and the data averaged. Compound was administered intravenously (either bolus injection of approximately 5 seconds or infusion of 15 minutes duration), and data were recorded every 1 minute for 60 minutes post compound administration. Data are calculated as either the peak change in heart rate or mean arterial pressure or are calculated as the area under the curve for changes in heart rate or blood pressure versus time. Data are expressed as mean±SEM. A one-tailed Student's paired t-test is used for statistical comparison to baseline values and considered significant at p<0.05.

The S1P effects on the rat cardiovascular system are described in Sugiyama, A., N. N. Aye, Y. Yatomi, Y. Ozaki, K. Hashimoto 2000 Effects of Sphingosine-1-Phosphate, a naturally occurring biologically active lysophospholipid, on the rat cardiovascular system. Jpn. J. Pharmacol. 82: 338-342, hereby incorporated by reference in its entirety.

Measurement of Mouse Acute Toxicity

A single mouse is dosed intravenously (tail vein) with 0.1 ml of test compound dissolved in a non-toxic vehicle and is observed for signs of toxicity. Severe signs may include death, seizure, paralysis or unconciousness. Milder signs are also noted and may include ataxia, labored breathing, ruffling or reduced activity relative to normal. Upon noting signs, the dosing solution is diluted in the same vehicle. The diluted dose is administered in the same fashion to a second mouse and is likewise observed for signs. The process is repeated until a dose is reached that produces no signs. This is considered the estimated no-effect level. An additional mouse is dosed at this level to confirm the absence of signs.

Assessment of Lymphopenia

Compounds are administered as described in Measurement of Mouse Acute Toxicity and lymphopenia is assessed in mice at three hours post dose as follows. After rendering a mouse unconscious by $CO_2$ to effect, the chest is opened, 0.5 ml of blood is withdrawn via direct cardiac puncture, blood is immediately stabilized with EDTA and hematology is evaluated using a clinical hematology autoanalyzer calibrated for performing murine differential counts (H2000, CARESIDE, Culver City Calif.). Reduction in lymphocytes by test treatment is established by comparison of hematological parameters of three mice versus three vehicle treated mice. The dose used for this evaluation is determined by tolerability using a modification of the dilution method above. For this purpose, no-effect is desirable, mild effects are acceptable and severely toxic doses are serially diluted to levels that produce only mild effects.

What is claimed is:

1. A compound represented by Formula II

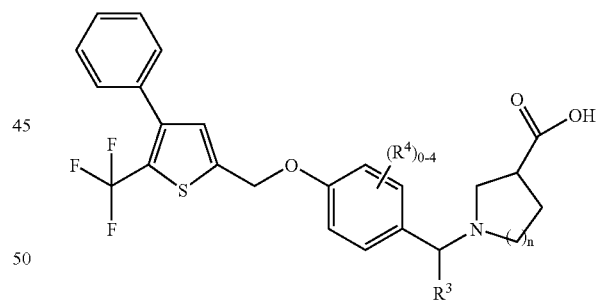

or a pharmaceutically acceptable salt or hydrate thereof, wherein:

n=0 or 1;

R$^3$ is selected from the group consisting of: hydrogen and C$_{1-4}$alkyl, optionally substituted with from one up to the maximum number of substitutable positions with a substituent independently selected from the group consisting of: halo and hydroxy;

each R$^4$ is independently selected from the group consisting of: halo, C$_{1-4}$alkyl and C$_{1-3}$alkoxy, said C$_{1-4}$alkyl and C$_{1-3}$alkoxy optionally substituted from one up to the maximum number of substitutable positions with halo.

2. The compound according to claim 1 wherein n is 0.

3. The compound according to claim 1 wherein n is 1.

4. The compound according to claim 1 wherein R³ is hydrogen.
5. The compound according to claim 1 selected from the following table:
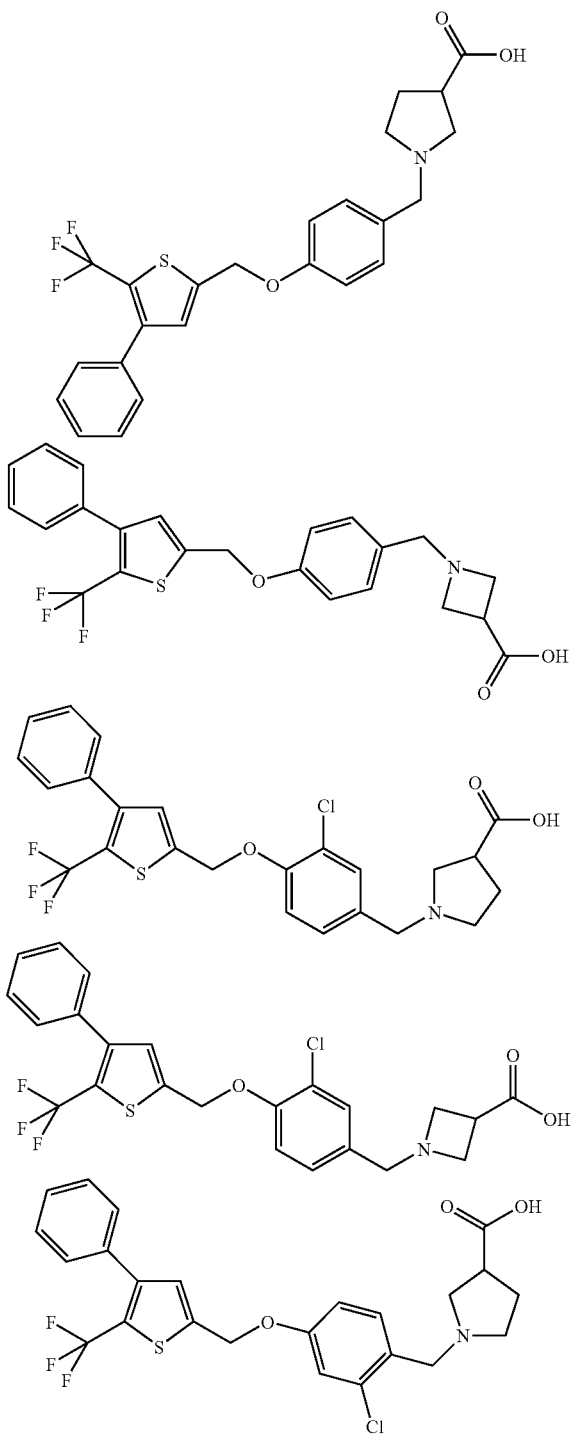
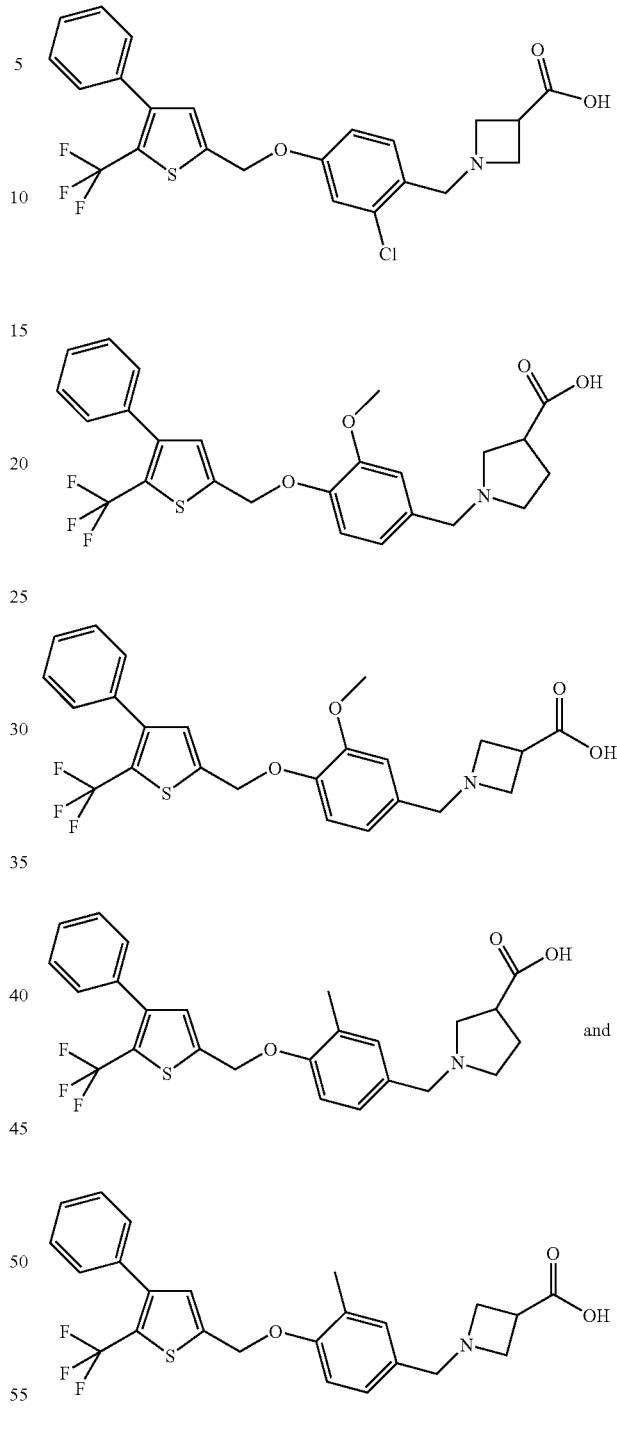
or a pharmaceutically acceptable salt of any of the foregoing compounds.
* * * * *